(12) United States Patent
Kohara et al.

(10) Patent No.: US 8,178,305 B2
(45) Date of Patent: May 15, 2012

(54) METHOD OF ANALYZING BIOCHEMICAL

(75) Inventors: Yoshinobu Kohara, Yokohama (JP);
Hideyuki Noda, Kokubunji (JP);
Teruyuki Kobayashi, Sendai (JP);
Kunihiro Suto, Hitachi (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 605 days.

(21) Appl. No.: 11/915,021

(22) PCT Filed: Feb. 10, 2006

(86) PCT No.: PCT/JP2006/302786
§ 371 (c)(1),
(2), (4) Date: Jul. 16, 2009

(87) PCT Pub. No.: WO2006/123459
PCT Pub. Date: Nov. 23, 2006

(65) Prior Publication Data
US 2009/0298094 A1    Dec. 3, 2009

(30) Foreign Application Priority Data
May 20, 2005    (JP) .................. 2005-147483

(51) Int. Cl.
*G01N 33/53* (2006.01)
(52) U.S. Cl. ........................ 435/7.1; 435/7.2; 436/518
(58) Field of Classification Search .................. None
See application file for complete search history.

(56) References Cited

U.S. PATENT DOCUMENTS

| | | | |
|---|---|---|---|
| 6,288,220 B1 * | 9/2001 | Kambara et al. | 536/24.31 |
| 6,559,296 B2 | 5/2003 | Suyama | |
| 7,141,658 B1 * | 11/2006 | Raoult et al. | 536/23.1 |
| 2002/0106682 A1 | 8/2002 | Lee et al. | |
| 2004/0191793 A1 | 9/2004 | Kitawaki et al. | |
| 2004/0229346 A1 | 11/2004 | Kohara et al. | |
| 2004/0235034 A1 * | 11/2004 | Kuno et al. | 435/6 |
| 2005/0008540 A1 | 1/2005 | Ishiguro et al. | |
| 2005/0130325 A1 * | 6/2005 | Oshida et al. | 436/528 |
| 2006/0275818 A1 | 12/2006 | Kambara et al. | |

FOREIGN PATENT DOCUMENTS

| | | |
|---|---|---|
| CN | 1464307 | 12/2003 |
| JP | 11-75812 | 3/1999 |
| JP | 11-243997 | 9/1999 |
| JP | 2000-346842 | 12/2000 |
| JP | 2004-333401 | 11/2004 |
| JP | 2004-361316 | 12/2004 |

(Continued)

OTHER PUBLICATIONS

Zhi et al. (Anal. Chem. 2003 vol. 75, p. 4125-4131).*

(Continued)

*Primary Examiner* — Jacob Cheu
(74) *Attorney, Agent, or Firm* — Antonelli, Terry, Stout & Kraus, LLP.

(57) ABSTRACT

A method of highly sensitive and quantitative luminescent analysis with the use of a detection device using a microchannel and carrying a molecule which is capable of capturing a substance to be detected and bonded to a solid phase. A biochemical to be detected is captured in a channel-type device having a probe bonded to a solid phase. After labeling for luminescence, a luminescent reagent is flown thereto and the luminescence in the vicinity of the probe is optically detected.

18 Claims, 20 Drawing Sheets

FOREIGN PATENT DOCUMENTS

| | | |
|---|---|---|
| KR | 2002-0064805 | 8/2002 |
| WO | WO 03/081243 | 10/2003 |

OTHER PUBLICATIONS

He et al. (Biosensor & Bioelectronics 2004 vol. 20 p. 460-467).*

Korean Official Action issued Oct. 7, 2009, for Application No. 10-2007-7028358.
Japanese Official Action dated Jun. 29, 2010, for Application No. 2007-516207.
Chinese Official Action dated Mar. 13, 2009, in Application No. 200680017513.7.

* cited by examiner

METHOD OF ANALYZING BIOCHEMICAL

TECHNICAL FIELD

The present invention relates to a method of analyzing a biochemical. The present invention also relates to an analyzer of a biochemical using an analysis device in which a probe, which is a substance capable of specifically capturing the biochemical, is immobilized on a solid phase.

BACKGROUND ART

The fluorescence method has conventionally been used for sensitive detection of a biochemical. Since this method is easy to utilize compared with a technique using a radioisotope adopted theretofore and no safety measure against radioactivity is needed, the technique was quickly replaced by the fluorescence method. The fluorescence method includes a method of directly labeling a biochemical to be detected with a fluorescent substance, and a method of indirect labeling. If a fluorescent immunological test is taken as an example, in the former method, a biochemical to be detected is directly labeled with a fluorescent substance and then a fluoresceinated biochemical is captured by an antibody immobilized on a solid phase for detection. The so-called competitive method is also included in this category. The latter method includes a sandwich assay in which an antibody having an affinity for the same biochemical is fluoresceinated to allow a secondary reaction.

On the other hand, the chemiluminescent assay has been developed. Since scattered excitation light is not measured as a background light in the case of chemiluminescence, more sensitive measurement can be performed. For chemiluminescence, a biochemical to be detected is directly or indirectly labeled with an enzyme or a fluorescent substance. For the former case, peroxidase or alkaline phosphatase is often used as an enzyme. The so-called enzyme-linked immunosorbent assay falls into this category. An antibody capable of capturing a biochemical to be detected is immobilized on a microplate wall or the like and then a solution containing a substance to be detected is added. The substance to be detected in the solution is captured by the antibody on the wall surface before an excessive solution is washed away. An enzyme labeled antibody for the substance to be detected is added thereto and, after waiting for the enzyme labeled antibody to bind to the substance to be detected, an excessive solution is washed away. Lastly, a solution containing a chemiluminescence reagent that reacts with the enzyme is poured in to detect generated luminescence. If a fluorescent substance is labeled with, for example, as an application of a detector of HPLC, each fluoresceinated molecule flowing out of the HPLC is mixed with a chemical excitation agent for reaction, to detect chemiluminescence emitted by the labeled fluorescent substance being chemically excited.

A technology of arranging beads (hereinafter called a beads array) to which a probe is bonded, in a tube (or capillary tube) is known as a detection device of multiple items (for example, Patent Document 1). Also, a detection device in which a microchannel is used and a molecule capable of capturing a target substance is bonded to a solid phase has been reported (for example, Patent Document 2).

Patent Document 1: Japanese Patent Application Laid-Open No. 11-243997
Patent Document 2: Japanese Patent Application Laid-Open No. 11-075812

DISCLOSURE OF THE INVENTION

In comparison with the fluorescence method, the number of photons received from a target in unit time becomes smaller in the luminescence detection method of chemiluminescence, bioluminescence and the like and thus, it is necessary to devise good ways such as using a highly sensitive measuring system and increasing the measuring time.

Capturing of a fluoresceinated substance, which is a substance to be detected and is fluoresceinated in advance, by a probe on a bead in a beads array has generally been used for fluorescence detection. While this method has an advantage of a faster reaction rate, there have been possibilities that scattered light originating from excitation light or background light from beads material could arise. Moreover, if luminescence detection is applied to a beads array, absolute sensitivity must be secured due to a smaller number of photons per unit time and, assumed is "crosstalk" in which luminescence from some bead being reflected by the surface of adjacent beads can be measured as if luminescence originating from adjacent beads. Even in a detection device in which a microchannel is used and molecules for capturing a target substance are bonded to a solid phase, scattered light or reflected light originating from luminescence may arise.

From what has been described above, a subject is to achieve a method of highly sensitive and qualitative luminescent detection using the flow of a solution in a detection device using a microchannel and having a molecule capable of capturing a substance to be detected bonded to a solid phase. Another subject is to prevent, in a beads array, crosstalk of luminescence between beads.

An analysis method of a biochemical that includes a probe bonded to a solid phase, a step of capturing a labeled substance to be detected by the probe or a step of capturing an unlabeled substance to be detected by the probe and labeling the substance, a step of supplying a chemiluminescence reagent by means of a liquid current, and a step of optically detecting a vicinity of a region where the chemiluminescence reagent and the labeling have reacted, is provided.

Here, the solid phase is a phase on which a probe is immobilized at least in part thereof. Particles (beads), a wall surface of a channel, a projection or a string-like member provided in a channel can be used as a solid phase.

Materials of the solid phase include plastics, metals, and inorganic compounds. Plastics include a styrene resin such as polystyrene and polymethyl styrene, a polyolefin resin such as polypropylene, polyethylene, and polycycloolefin, a (metha)acrylic resin such as polyacrylate including polycarbonate, polymethyl acrylate, and polyethyl acrylate and polymethacrylate including polymethyl methacrylate and polyethyl methacrylate, a fluorine contained resin such as polyfluoroolefin, and a silicone resin such as dimethylsiloxane and diethylsiloxane. Metals include, for example, iron, stainless, copper, or an alloy of these metals. Inorganic compounds include, for example, glass, ceramics, and semiconductors. However, materials of the solid phase are not limited to these and further, the solid phase may be formed of one material or a plurality of materials. Polystyrene is particularly preferable because of readiness of a probe for the solid phase, low background, and easy availability.

If a bead is used for the present invention, the bead diameter is preferably 0.1 µm to 6 mm, more preferably 0.5 µm to 1 mm, still more preferably 0.75 µm to 500 µm, and most preferably 1.0 µm to 100 µm. A tube into which beads should be put is a tube in accordance with the size of the beads and preferably has a diameter less than twice the bead diameter.

In a luminescence detection system, high sensitivity can be achieved by making measurements, with the timing of feeding a luminous substrate being set in line with that of measurement. Here, a phenomenon in which a high luminescence peak appears in a short time after a luminous substrate reaches the solid phase, for example, an enzyme on a bead is used. By observing the peak portion, it becomes possible to separate a signal from noise with a high degree of accuracy, leading to high-sensitivity measurement. In a method in which luminescence is measured while a chemiluminescence reagent is being flown, the chemiluminescence reagent is always supplied and concentrations of the chemiluminescence reagent do not decrease in the vicinity of an enzyme and therefore, long-time measurements can be made with stability while a decrease in luminescence intensity being controlled. Highly sensitive measurements can also be made with stability by adding signals after a high peak for a long time. If a large amount of substance to be detected is captured and concentrations of the enzyme are high, high-precision measurement can be made because a chemiluminescence reagent is supplied by a flow and a decrease in concentration in the vicinity of the chemiluminescence reagent can thereby be controlled. Also in a system in which measurement is made by having a photomultiplier tube scanned, high-precision measurement is enabled by setting up a slit and appropriately setting the relationship between the size of a bead to be measured and the slit to increase the resolution. A plurality of beads must be identified to determine a bead signal and thus, a certain level of spatial resolution is needed. Consideration including an influence of measurement bands shows that there are limitations such as an appropriate slit width in accordance with a measuring time and the like. There is also a means for increasing sensitivity and identifying beads by maintaining a space between beads to be measured and adopting a broad slit width.

The luminescence detection system in the present invention includes a chemiluminescence detection system and a bioluminescence detection system. Chemiluminescence is a phenomenon in which molecules excited by a chemical reaction emit light as energy when returning to the ground state, and bioluminescence is a phenomenon in which light is emitted by a chemical reaction such as oxidizing a luminescent substance using a biological enzyme such as luciferase of fireflies or bacteria, and may in the broad sense fall under the category of chemiluminescence. The chemiluminescence detection system includes a detection system using chemiluminescence of peroxidase using luminol/hydrogen peroxide as a substrate, a detection one using chemiluminescence of alkaline phosphatase using adamantyl methoxyphosphoryl phenyldioxetane (AMPPD), which is a dioxetane derivative, as a substrate, and a detection one using chemiluminescence of alkaline phosphatase by means of a peroxyoxalate derivative such as bis(2,4,6-trichlorophenyl) oxalate (TCPO)/hydrogen peroxide/fluorescent dye such as 8-anilinonaphthalenesulfonic acid (ANS). The bioluminescence detection system includes, for example, a bioluminescence detection system of firefly luciferase using ATP/luciferin/magnesium ions as substrates, a detection one for detecting NADH generated by glucose-6-phosphate dehydrogenase using glucose-6-phosphate/NAD as substrates by means of a luminescent reaction of bacterial luciferase and NADH-FMN-oxidoreductase, and a detection one for detecting ATP generated by pyruvate kinase using ADP and phosphoenolpyruvate as substrates by means of a luminescent reaction of luciferin-luciferase of fireflies.

The subject of preventing crosstalk of luminescence between beads is important for sensitive detection of multiple items regardless of optical settings for measurement. A means for solving this subject is to place a bead made of material having a light blocking effect among a plurality of beads to be measured. Another means for solving the subject is to bring the refractive index of a solution containing a chemiluminescence reagent closer to that of beads. If a solution containing a chemiluminescence reagent is ideally prepared and has substantially the same refractive index as that of bead material, light is not reflected on the surface of beads and thus, reflection of light between beads, that is, crosstalk can be prevented. Still another means for solving this subject is to insert a polarizing plate between a measuring apparatus and a beads array. While luminescence on the surface of beads is considered not to be polarized because the luminous substrate emits light in random directions, crosstalk reflected by adjacent beads is considered to be polarized because of a difference between the reflectance of s waves and that of p waves. Thus, crosstalk components can predominantly be blocked by inserting a polarizing plate and, as a result, a contribution of crosstalk can be made smaller.

An example of an analysis method includes a step of supplying a liquid containing a labeled substance to be detected or an unlabeled substance to be detected to a channel containing a solid phase to which a probe is bonded at least in part thereof, a step of causing the probe to capture the labeled substance to be detected or a step of causing the probe to capture the unlabeled substance to be detected to label the unlabeled substance, a step of supplying a reagent for a luminescent reaction to the channel by means of a liquid flow, and a step of optically detecting a vicinity of a region where the reagent for the luminescent reaction and the labeling have reacted.

An example of an analysis kit includes a capillary tube, a first particle on which a probe is immobilized and which is contained in the capillary tube, a second particle which contains light blocking material and is contained in the capillary tube, and a reagent for a luminescent reaction.

An example of an analyzer includes a liquid feeding part for introducing a liquid into or drawing it out of a capillary tube containing a solid phase on which a probe is immobilized at least in part thereof, a first container for containing a sample, a second container for containing a reagent for a luminescent reaction, and a detection part for optically detecting an arbitrary region of the solid phase, wherein the first container and the second container are connected to the liquid feeding part.

According to the present invention, there is an effect of being able to realize a highly sensitive and quantitative luminescence method for a detection device that performs luminescence detection in multiple items. Particularly when a beads array is used, there is further an effect of preventing crosstalk of luminescence between beads.

In the case of luminescence detection on multiple items, a method of adding a reagent to each of holes of, for example, a microplate has been used. Compared with such a system, a beads array can perform simple and uniform reactions without the need for pouring distributively and the like because solutions containing target substances and luminous substrates can be flown successively. Moreover, in contrast to the microplate, the reaction area is not separated by a wall or the like for each item and thus, only a small amount of reagent is needed for luminescence detection.

EXPLANATIONS OF REFERENCE NUMERALS

Figure 1:
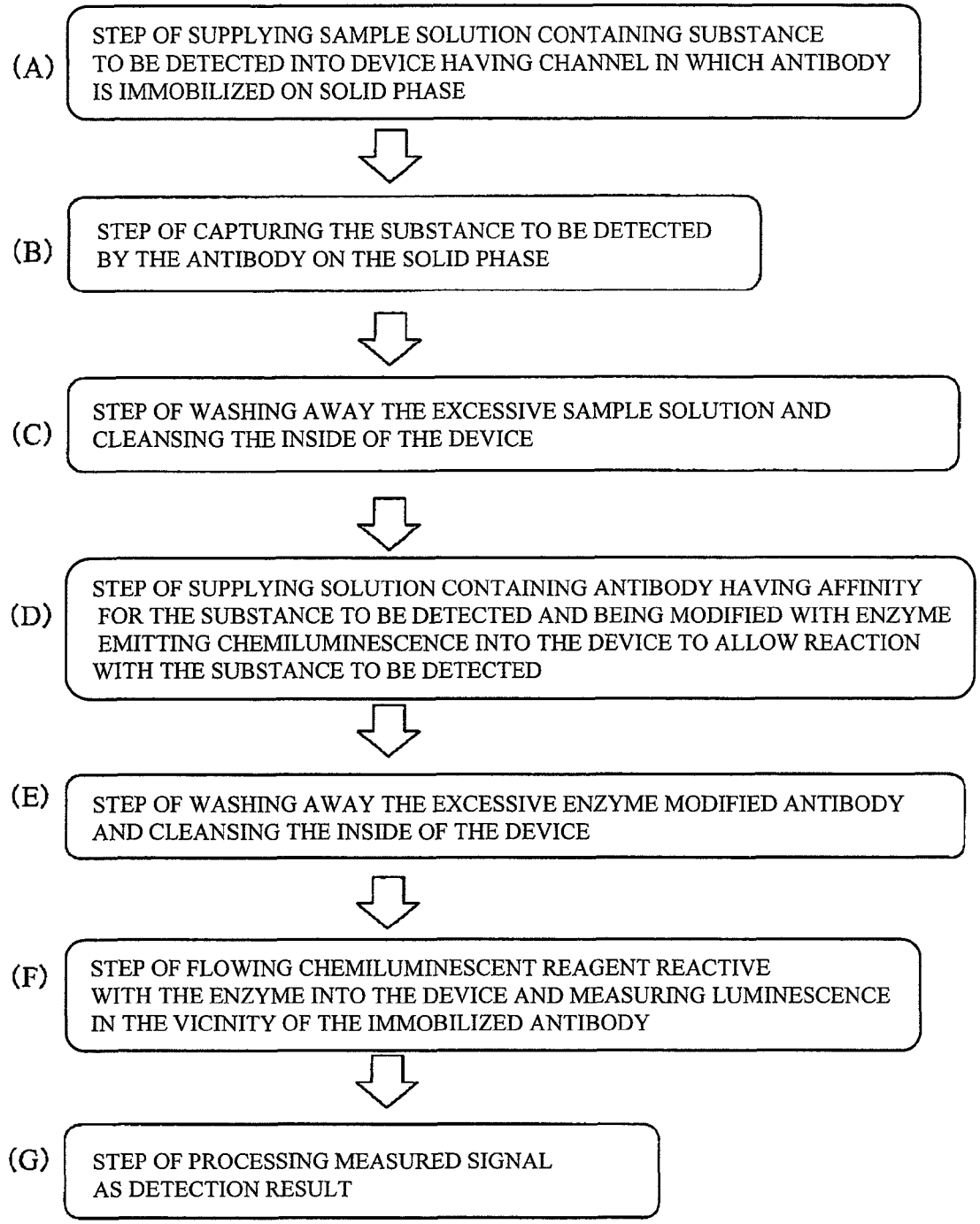
FIG. 1 is a flow chart of an embodiment of the present invention.

101: Capillary
102: Bead to which an antibody is bonded
103: Bead to which no antibody is bonded
104: Anti-α-fetoprotein antibody
105: α-fetoprotein
106: HRP labeled anti-α-fetoprotein antibody
107: Chemiluminescence reagent
108: Luminescence
109: Sample solution containing α-fetoproteins
110: Cleansing buffer
111: Solution containing the HRP labeled anti-α-fetoprotein antibody 106
112: Cleansing buffer
113: Solution containing a chemiluminescence reagent
114: Optical measuring apparatus
121: Beads array
121a: Beads array
121b: Beads array
121c: Beads array
121d: Beads array
122: Capillary
122a: Connection part
122b: Connection part
122c: Connection part
123: Syringe
124: Syringe pump
125: Capillary
126: Valve
127: Container
131: Optical fiber
132: Connection connector to PMT
133: PMT
134: Line
135: Personal computer
136: Particle (Beads) stopper
137: Connection part (inner seal connector)
141: Beads array
142: Optical fiber bundle
143: Connection connector to PMT
144: Detection area
151: Beads array
152: Objective lens
153: Imaging lens
154: Slit
155: PMT
156: Optical system
157: Line
158: Personal computer
201: Beads array group
202: Liquid feeding system
203: Solution holding part and connection switching part
204: Camera lens
205: CCD camera
206: Line
207: Personal computer
208: Measured portion
211: Luminescent bead
212: Bead from which no luminescence is expected
213: Capillary
214: Aqueous solution containing a chemiluminescence reagent
221: Light blocking bead
231: Light beam directly directed toward an optical system
232: Light beam directed toward adjacent beads
233: Solution whose refractive index is adjusted
241: Polarizing plate

BEST MODE FOR CARRYING OUT THE INVENTION

FIG. 1 is a flow chart showing an outline of an analysis method in a first embodiment. Details will be described in the next and subsequent paragraphs. As the first step (A), a sample solution containing a substance to be detected is introduced into a device having a channel in which an antibody capable of capturing a biochemical to be detected is immobilized on a solid phase. Nothing is captured by the antibody before the sample is introduced. As the next step (B), there exists a step of capturing the substance to be detected in the sample solution by the antibody on the solid phase. In this case, feeding of the sample solution can be continued or stopped to wait and see how a reaction proceeds. As the subsequent step (C), there exists a step of washing away an excessive sample solution to cleanse the inside of the device. By cleansing the inside of the device, the substance to be detected will substantially exist only in a region where the substance is captured by the antibody. As the subsequent step (D), there exists a step of introducing a solution containing an antibody having an affinity for the substance to be detected and labeled with an enzyme causing luminescence, into the device to allow a reaction of the antibody with the substance to be detected. This step is a step of indirectly labeling the substance to be detected. As the subsequent step (E), there exists a step of washing away excessive enzyme labeled antibodies that have not reacted with the substance to be detected and thus have been not captured by the solid phase, to cleanse the inside of the device. By cleansing the inside of the device, the enzyme to cause luminescence later will substantially exist only in a region where the substance to be detected exists, that is, in a region where the antibody to capture the biochemical to be detected has been immobilized on the solid phase and therefore, luminescence will not be caused in other places. As the subsequent step (F), there exists a step of flowing a chemiluminescence reagent that reacts with the enzyme into the device, to measure luminescence in the vicinity of the antibody. Since the enzyme that causes luminescence exists only in places where the substance to be detected has been captured, luminescence in the vicinity of the solid phase on which the enzyme to capture the substance to be detected is immobilized can be considered to result from the existence of the substance to be detected. The amount of luminescence also reflects that of the captured substance to be detected and, as a result, the amount or concentrations of the substance to be detected in the sample solution. As the last step (G), there exists a step of processing measured signals originating from luminescence as detection results. Based on this step, the amount of the substance to be detected will be estimated from the obtained intensity of luminescence.

Figure 2:
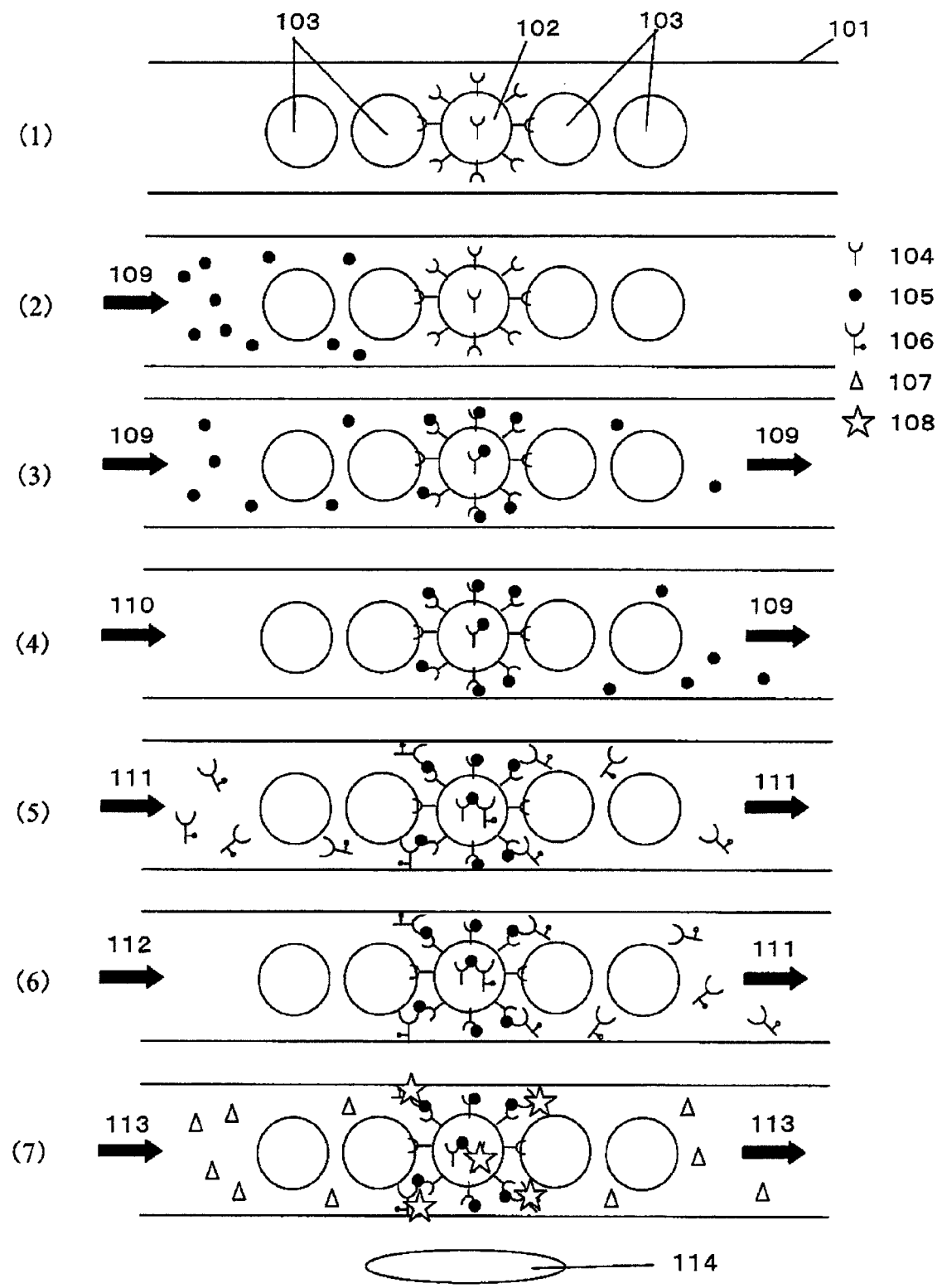
FIG. 2 is a schematic diagram of the embodiment of the present invention.

FIG. 2 shows an outline of the first embodiment as a schematic diagram in the vicinity of a solid phase on which a substance to be detected is immobilized. An overview of a liquid feeding apparatus and a measuring apparatus will be provided in the next and subsequent paragraphs. In the present embodiment, an example in which a beads array is used as a device having a channel in which an antibody is immobilized on a solid phase is shown. FIG. 2(1) is a partially enlarged view of an outline of beads array. A capillary 101 is used for forming a channel. A bead 102 to which antibodies capable of capturing a detection target are bonded and beads 103 to which no antibody is bonded are arranged inside the capillary 101. The detection target in the present embodiment is, for example, an α-fetoprotein 105 and, for example, anti-α-fetoprotein antibodies 104 are immobilized on the bead 102. The inside diameter of the capillary is, for example, 150 μm, the diameter of the beads 102 and 103 is, for example, 100 μm, and material thereof is, for example, polystyrene. FIG. 2(2) shows a schematic diagram when a sample solution 109 containing the α-fetoprotein 105 has fed. It is tentatively assumed that the volume of the sample solution here is 50 μL and the volume flow rate of the solution is 10 μL per minute. Next, FIG. 2(3) shows how the α-fetoproteins 105 are captured by the anti-α-fetoprotein antibodies on the bead 102. In the beads array, the solution is forced to flow in a narrow space and turbulence is caused in the flow, resulting in a higher rate of liquid-solid reaction. To further enhance this effect, the α-fetoproteins are captured while the sample solution 109 being flown. A syringe pump, for example, is used for liquid feeding, as will be shown later, and the sample solution was fed reciprocatingly for reaction. Any mechanism that can send a liquid can be used for liquid feeding. A peristaltic pump or the like can also be used for another liquid feeding mechanism. The reaction time is, for example, 20 minutes. FIG. 2(4) shows a schematic diagram in which the sample solution 109 is cleansed by a cleansing buffer 110. A phosphate buffer (pH 7.4) containing, for example, salt was used as the cleansing buffer 110 and the sample solution 109 was cleansed under the conditions of flowing 100 μL in 30 seconds. Any other buffer that is normally used can also be used, including a carbonate buffer, an MES (2-(N-Morpholino) ethanesulfonic acid) buffer, a tris-hydroxy-aminomethane (hereinafter referred to as Tris)-ethylenediaminetetraacetic acid (hereinafter referred to as EDTA) buffer, a Tris-EDTA-boric acid buffer, and a boric acid buffer. Further, salt to be added that can be used includes sodium chloride, potassium chloride, ammonium chloride, sodium acetate, potassium acetate, and ammonium acetate. With this cleansing, the α-fetoproteins 105 that have not been captured onto the bead 102 are washed away from inside the beads array device.

FIG. 2(5) shows a schematic diagram in which a solution 111 containing an HRP (horseradish peroxidase) labeled anti-α-fetoprotein antibody 106 is fed into the beads array. HRP is used as a label, but in the present invention, labeling enzymes other than HRP and labeling other than enzymes can also be used. Labeling enzymes used in the present invention include, for example, peroxidase, alkaline phosphatase, glucose oxidase, β-D-galactosidase, glucose-6-phosphate dehydrogenase, invertase, adenosine triphosphate (hereinafter referred to as ATP) ase, luciferase, and aequorin.

It is tentatively assumed that the concentration of the HRP labeled anti-α-fetoprotein antibody 106 is 100 ng/ml, the volume of the solution 111 is 50 μL, and the volume flow rate is 10 μL per minute. The HRP labeled anti-α-fetoprotein antibody 106 reacts with the α-fetoprotein 105 captured by the anti-α-fetoprotein antibody 104 on the bead 102 and is captured, as a result, onto the bead 102. FIG. 2(6) shows a schematic diagram in which the HRP labeled anti-α-fetoprotein antibody solution 111 is cleansed by a cleansing buffer 112. A phosphate buffer (pH 7.4) containing, for example, salt was used as the cleansing buffer 112 and the solution 111 was cleansed under the conditions of flowing 100 μL in 30 seconds. With this cleansing, excessive HRP labeled anti-α-fetoprotein antibodies 106 that have not been captured onto the bead 102 are washed away from inside the beads array device.

Lastly, FIG. 2(7) shows a schematic diagram in which a solution 113 containing a reagent 107 for a luminescent reaction is flown into the beads array to measure luminescence 108. If an enzyme is used for labeling, the reagent 107 for the luminescent reaction must contain a substrate corresponding to the enzyme used. The substrate includes, for example, luminol, dioxetane, peroxyoxalate, glucose, β-D-galactosyl, glucose-6-phosphate, lucigenin, ascorbic acid phosphate, adenosine triphosphate, luciferin, or derivatives thereof, and calcium ions. The reagent for a luminescent reaction may contain hydrogen peroxide, an oxidizing agent such as peracid including alkyl hydroperoxide such as tert-butyl hydroperoxide, and an oxidizing agent of oxygenated additive oxidant such as iodosobenzene. The reagent for a luminescent reaction may further contain an enhancer. The enhancer includes, for example, a phenol derivative such as 4-iodophenol, 4-bromophenol, 4-chlorophenol, 4-phenylphenol, phenolindole, 2-chloro-4-phenylphenol, 4-(2'-thienyl)phenol, 4-(2'-benzothiazolyl)phenol, 4-[4'-(2'-methyl) thiazolyl] phenol, 4-[2'-(4'-methyl) thiazolyl] phenol, 4-(4'-thiazolyl) phenol, 4-[4'-(2'-(3'-pyridyl)) thiazole] phenol, phenothiazine-N-propylsulfonate, 3-(10-phenothiazine)-n-propylsulfonic acid, 3-(10-phenothiazine)-propylsulfonic acid, and p-hydroxy phenylpropionic acid, a thiazole derivative such as 6-hydroxyl benzoic thiazole and 4-(4-hydroxyl phenyl) thiazole, and diethylaniline.

If, for example, HRP is used as a labeling enzyme, for the reagent used for a luminescent reaction, luminol or a derivative thereof can be used as a substrate, lucigenin/hydrogen peroxide or the like as an oxidizing agent, and 4-iodophenol, 4-[4'-(2'-methyl) thiazolyl] phenol, 4-[2'-(4'-methyl) thiazolyl] phenol, 4-(4'-thiazolyl)phenol, 4-[4'-(2'-(3'-pyridyl)) thiazole] phenol, 4-(2'-thienyl)phenol, phenothiazine-N-propylsulfonate, and phenol indophenol, and preferably 4-[4'-(2'-methyl) thiazolyl] phenol or 4-[2'-(4'-methyl) thiazolyl] phenol as an enhancer.

In the present invention, other labeling and combinations of reagents for a luminescent reaction can also be used. For example, such a chemiluminescence detection system includes a system in which glucose oxidase is used as a labeling enzyme and glucose/a peroxyoxalate derivative such as bis(2,4,6-trichlorophenyl) oxalate (TCPO)/fluorescent dye such as 8-anilinonaphthalenesulfonic acid (ANS), or glucose/isoluminol/micro-peroxidase (m-POD) as reagents for a luminescent reaction, a system in which alkaline phosphatase (ALP) is used as a labeling enzyme and a dioxetane derivative such as adamantyl methoxyphosphoryl phenyldioxetane (AMPPD) as a reagent for a luminescent reaction, a system in which β-D-galactosidase is used as a labeling enzyme and o-nitrophenyl-β-D-galactosyl/galactose dehydrogenase/NAD+/NADH or lactose/glucose oxidase (GOD)/isoluminol/m-POD, or lactose/GOD/TCPO/ANS as reagents for a luminescent reaction, a system in which glucose-6-phosphate dehydrogenase is used as a labeling enzyme and glucose-6-phosphate/NAD (P)+/NAD (P) H as reagents for a luminescent reaction, and a system in which invertase is used as a labeling enzyme and saccharose/lucigenin/OH— as reagents for a luminescent reaction. Such a bioluminescence detection system includes a system in which firefly luciferase is used as a labeling enzyme and ATP/luciferin/magnesium ions as reagents for a luminescent reaction, a system in which ALP is used as a labeling enzyme and luciferin-O-phosphate/ATP as reagents for a luminescent reaction, a system in which acetate kinase is used as a labeling enzyme and acetyl phosphate/alcohol dehydrogenase (ADP)/luciferin/luciferase as reagents for a luminescent reaction, a system in which glucose-6-phosphate dehydrogenase is used as a labeling enzyme and glucose-6-phosphate/NAD/bacterial luciferase/NADH-FMN-oxidoreductase as reagents for a luminescent reaction, and a system in which pyruvate kinase is used as a labeling enzyme and ADP/phosphoenolpyruvate/firefly luciferin/luciferase as reagents for a luminescent reaction.

The volume flow rate of the solution 113 containing the reagent 107 for a luminescent reaction was set at 10 µL per minute and the solution was continuously flown for 10 minutes or longer. The luminescence 108 is caused by a reaction of HRP on the HRP labeled anti-α-fetoprotein antibody 106 with the reagent 107 for a luminescent reaction and therefore, luminescence occurs only in the vicinity of the bead 102. That is, HRP is bonded to the bead via the antibody immobilized on the bead for capturing a detection target, the detection target captured by the antibody, and the HRP labeled anti-α-fetoprotein antibody 106 captured by the detection target and luminescence occurs in the vicinity of HRP, which is a label, resulting in luminescence in the vicinity of the surface of the one bead 102. The luminescence 108 is measured using an optical measuring apparatus 114. Details of the optical measuring apparatus 114 will be provided later.

Figure 3:
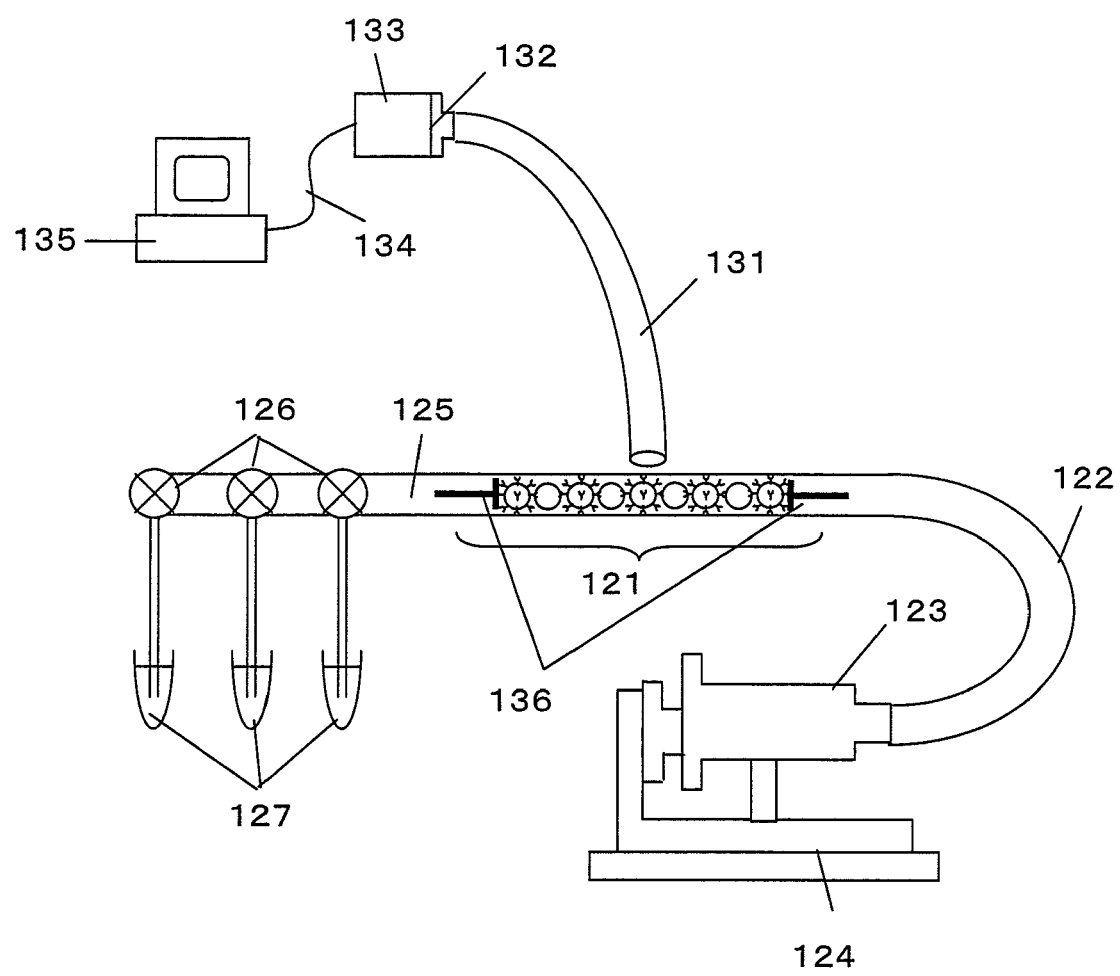
FIG. 3 is a schematic diagram of an apparatus in the embodiment of the present invention.

FIG. 3 shows an apparatus outline in the first embodiment. A beads array 121 described in FIG. 2 is arranged in the center and capillaries 122 and 125 are provided on both sides thereof. One side of the beads array is connected to a syringe 123 via the capillary 122. When a syringe pump 124 is operated, a piston of the syringe 123 is pushed and pulled and, as a result, a liquid can be fed into the beads array 121. The capillary 125, which is connected to a plurality of containers 127 via valves 126, is provided on the other end of the beads array 121. Each of the plurality of containers 127 contains a sample solution, a cleansing buffer, an HRP labeled antibody solution and the like already described using FIG. 2 in the preceding paragraphs and is also used as a waste liquid reservoir. Each of the containers 127 is accessed by operating the valve 126. Luminescence in the beads array 121 is measured through an optical fiber 131. One end of the optical fiber 131 is arranged closer to luminescent beads in the beads array 121 by an XY stage (not shown). The other end of the optical fiber 131 is connected to a PMT 133 through a connector 132 to the PMT (photomultiplier tube). With this configuration, luminescence from the beads array 121 collected by the optical fiber 131 is guided to the PMT 133 for measurement. A signal from the PMT 133 is output to a personal computer 135, which is a data processing apparatus, through a line 134. Data processing is performed in the personal computer 135.

Figure 4A:
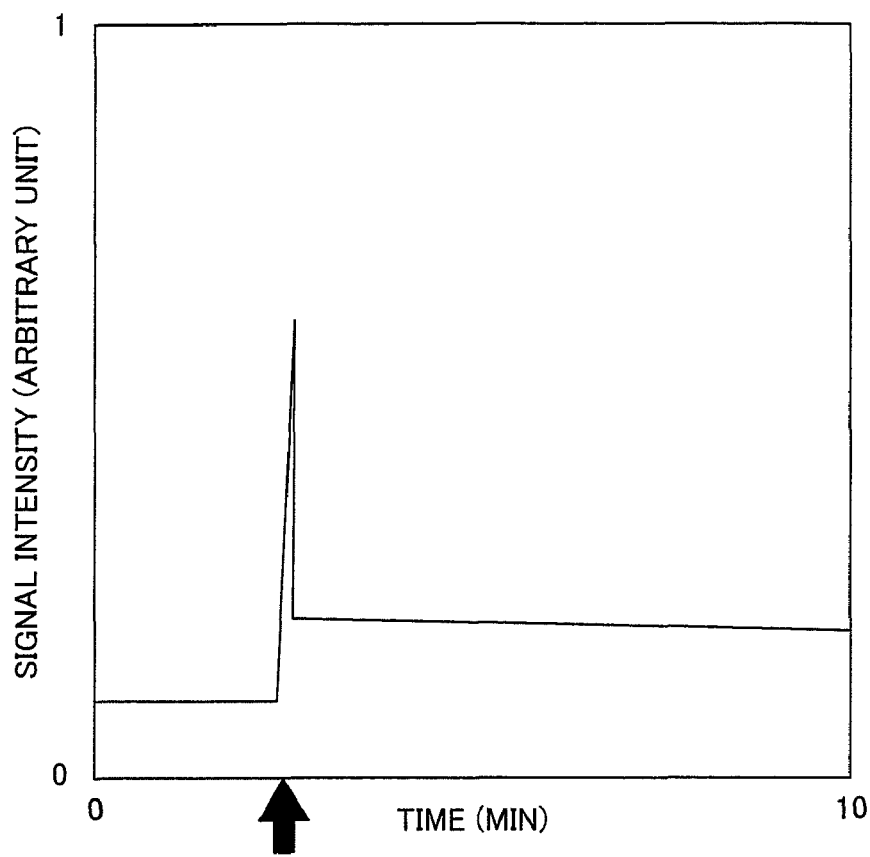
FIG. 4A and FIG. 4B are a luminescence measurement example and an outline of liquid feeding timing of a chemiluminescence reagent in the embodiment of the present invention.
Figure 4B:
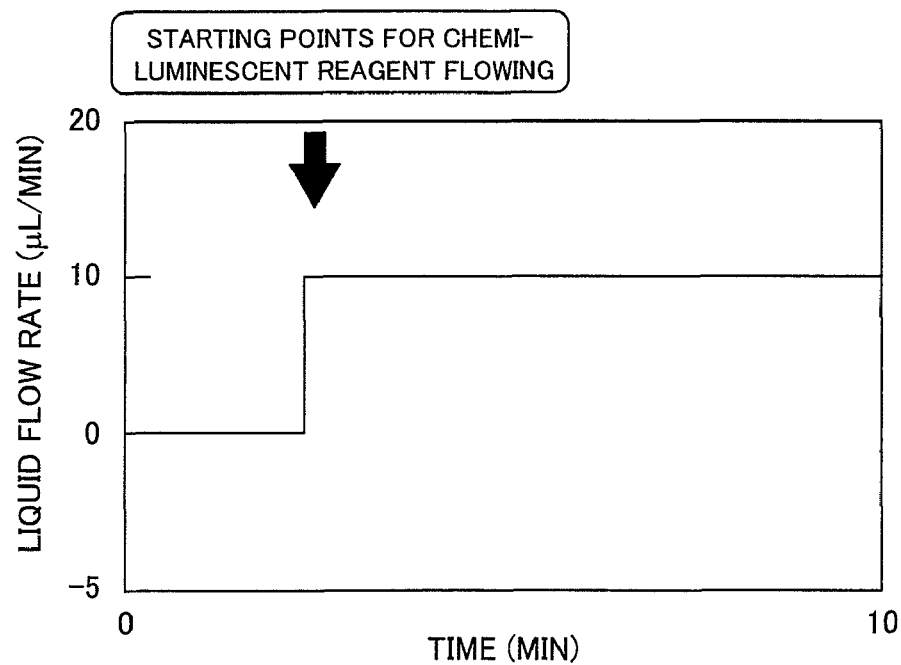

FIG. 4A is a luminescence measurement result example in the first embodiment and FIG. 4B is an outline of timing of chemiluminescence reagent feeding and the amount of liquid fed. Measurement starts at time 0 and, at this point, no chemiluminescence reagent has been fed and thus, no luminescence is measured. Signal intensity remains constant at a background level. A solution containing a chemiluminescence reagent is fed at the volume flow rate of 10 µL per minute in timing of the start of chemiluminescence reagent feeding and the feeding is continued. Signal intensity due to luminescence drops immediately after a high peak is temporarily recorded. After dropping, the signal intensity decreases very slowly. The peak width of the first high peak is about 1 second or less. The appearance of this timing specific peak is a phenomenon observed specifically in luminescence. In a conventional method, luminescence is measured by putting a chemiluminescence reagent into a container and then setting the container to a luminescence measuring apparatus, and so this timing specific peak has not been measured. The timing specific peak can be measured by measuring luminescence at a region where luminescence occurs while a reagent for a luminescent reaction is being flown. By measuring the timing specific peak, measurement with high S/N can instantaneously be made. Moreover, as a result thereof, measurement can be made with a smaller amount of chemiluminescence reagent. Further, highly sensitive measurement can be made. According to a method in which luminescence is measured while a reagent for a luminescent reaction being flown, the chemiluminescence reagent is always supplied and the concentration of the chemiluminescence reagent in the vicinity of an enzyme does not decrease and therefore, long-time measurements can be made with stability while a decline in luminescence intensity being controlled. Highly sensitive measurements can also be made with stability by integrating signals after a high peak for a long time. For example, by acquiring output from the PMT 133 at sampling intervals of 1 millisecond and integrating the digital data in the personal computer 135, a result with higher signal to noise ratio than when sampled at one point can be obtained. If signal attenuation is small and can be ignored, the signal to noise ratio can be considered to improve in proportion to a square root of the number of integration points. If a large amount of substance to be detected is captured and concentrations of the enzyme is high, high-precision measurement can be made because a chemiluminescence reagent is supplied by a flow and a decrease in concentration in the vicinity of the chemiluminescence reagent can thereby be controlled.

The phenomenon in which the timing specific peak appears can be interpreted and understood as follows. In the initial timing of feeding a chemiluminescence reagent, luminescence occurs on a large scale because the chemiluminescence reagent that has not been around an enzyme on the beads advances toward the enzyme at a dash. The concentration of the chemiluminescence reagent around the enzyme at that instant is the same as that of the fed chemiluminescence reagent solution and is substantially maximal. Once a reaction is started, the chemiluminescence reagent is consumed in an area of thin liquid film in the vicinity of the surface of beads, with the concentration of the chemiluminescence reagent lowering. Thus, after the peak, the luminescent intensity drops. Subsequently, the luminescent intensity is considered to be observed at an approximately constant level where both the speed at which the chemiluminescence reagent carried by a flow diffuses into the thin liquid film and the speed at which the chemiluminescence reagent is consumed on the surface are balanced. It is advantageous to flow a solution containing the chemiluminescence reagent compared with stopping the flow of the solution, because the thin liquid film is thin and thus, the diffusion length is short. Moreover, as a matter of course, supplying the chemiluminescence reagent with the flow can prevent bulk concentrations of the chemiluminescence reagent from lowering due to consumption of the chemiluminescence reagent and is advantageous to long-time measurement. It is naturally possible to stop feeding a chemiluminescence reagent solution after flowing the chemiluminescence reagent, and detection of luminescence can still be performed. Also in this case, advantageous measurement can be performed by feeding the chemiluminescence reagent and measuring luminescence simultaneously.

A beads array is used in the present embodiment, but the present invention is not limited to the use of a beads array. The present invention can generally be applied when, in a device having a channel in which a probe for capturing a biochemical to be detected is immobilized on a solid phase, luminescence is detected by measuring vicinities of an area where the probe is immobilized. Antibody immobilizing beads are used in the present embodiment to perform a sandwich assay of proteins, but the present invention is not limited to this.

Probes to be immobilized generally include deoxyribonucleic acid (DNA), ribonucleic acid (RNA), peptide nucleic acid (PNA), and also artificial nucleobase having adenine, thymine, cytosine, guanine, uridine, and inosine and nucleic acid derivatives. Probes are preferably those that can capture complementary molecules, such as those mentioned above, peptides, glycopeptides, proteins, glycoproteins, polysaccharide and chemical synthesis polymers, but are not limited to these.

If a nucleic acid probe is used, the present invention can be applied to nucleic acid detection and further, if a protein probe is used, the present invention can be used also for antibody test and antigen test and can be applied, for example, to food allergy testing, specific IgE allergy test, screening for infectious diseases, analysis of specified chemical substance, and pollutant analysis. Further, a sugar-lectin reaction and a receptor can also be used as a probe. A probe using interactions between DNA and proteins can be designed and further can be applied to an enzyme-substrate reaction, for example, a biotin-avidin reaction.

Figure 5:
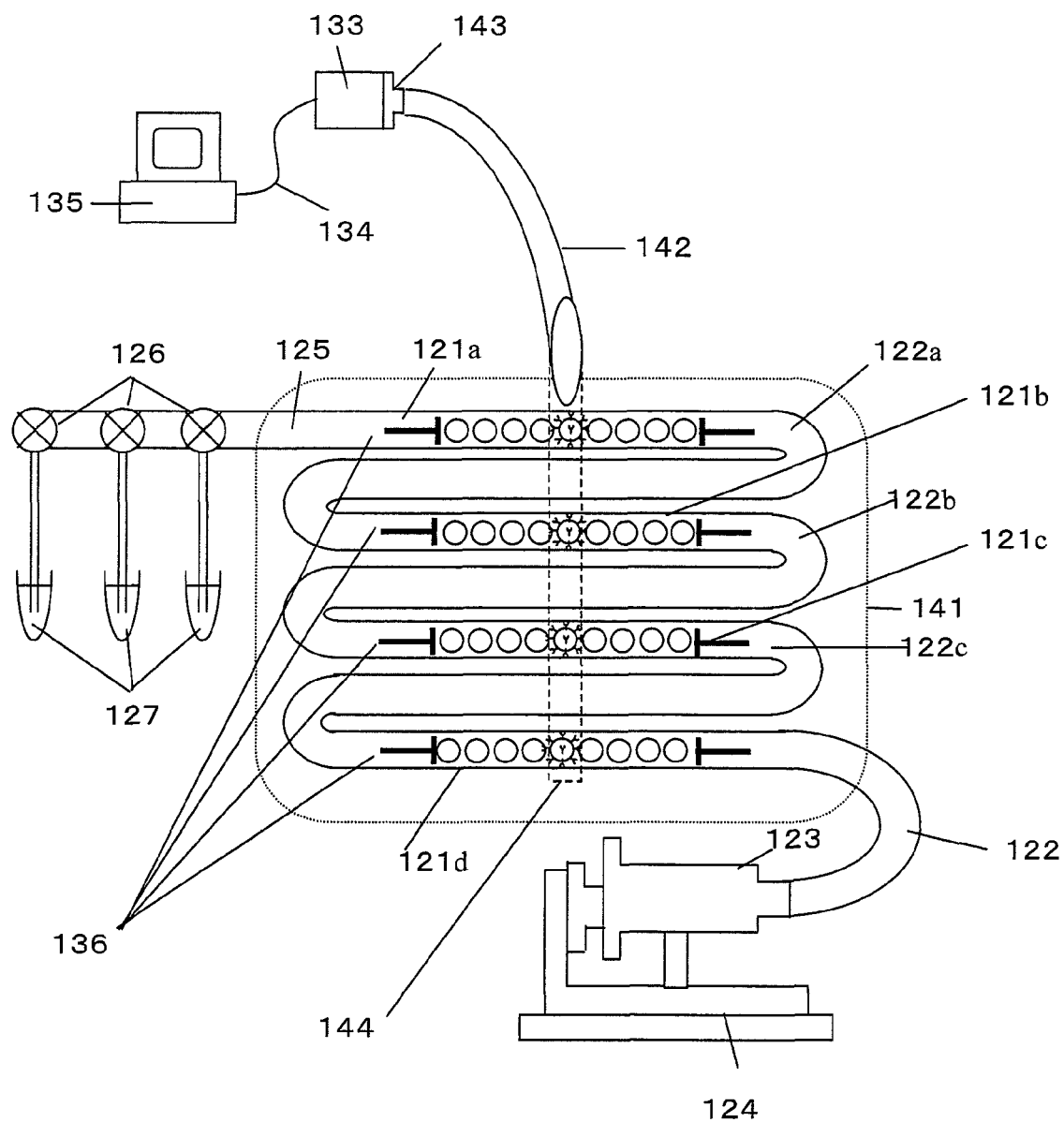
FIG. 5 is a schematic diagram of an apparatus in an embodiment of the present invention.

FIG. 5 shows an apparatus outline in a second embodiment. In comparison with the apparatus described in FIG. 3, the beads array and the optical fiber have been modified. A beads array 141 shown in FIG. 5 has a form in which a plurality (here four) of what corresponding to the beads array 121 in FIG. 2 are connected and each of the bead portions is arranged so that they all are immediately below a large-diameter optical fiber bundle 142. The diameter of the optical fiber bundle 142 is preferably equal to or larger than an area in which beads to be measured are arranged and at least in this configuration, it is assumed that the diameter of the optical fiber bundle 142 is equal to or larger than the outside diameter of beads corresponding to measurement items in one beads array, that is, the outside diameter of beads to be detected on which a probe is immobilized (when there are a plurality of beads, a length obtained by adding the outside diameters of the plurality of beads). Beads to be measured can thereby be reliably detected. The internal volume of connection parts 122a, 122b, and 122c was each temporarily set to be about 10 µL. Each of beads arrays 121a, 121b, 121c, and 121d corresponding to the beads array 121 contains beads on which different antibodies, for example, an anti-α-fetoprotein antibody, an anti-CA19-9 antibody, an anti-CEA antibody, and an anti-PSA antibody are immobilized. The optical fiber bundle 142 is connected to the PMT 133 through a connection connector 143 of the optical fiber bundle and PMT. Otherwise, the apparatus configuration is the same as that in FIG. 2.

Figure 6A:
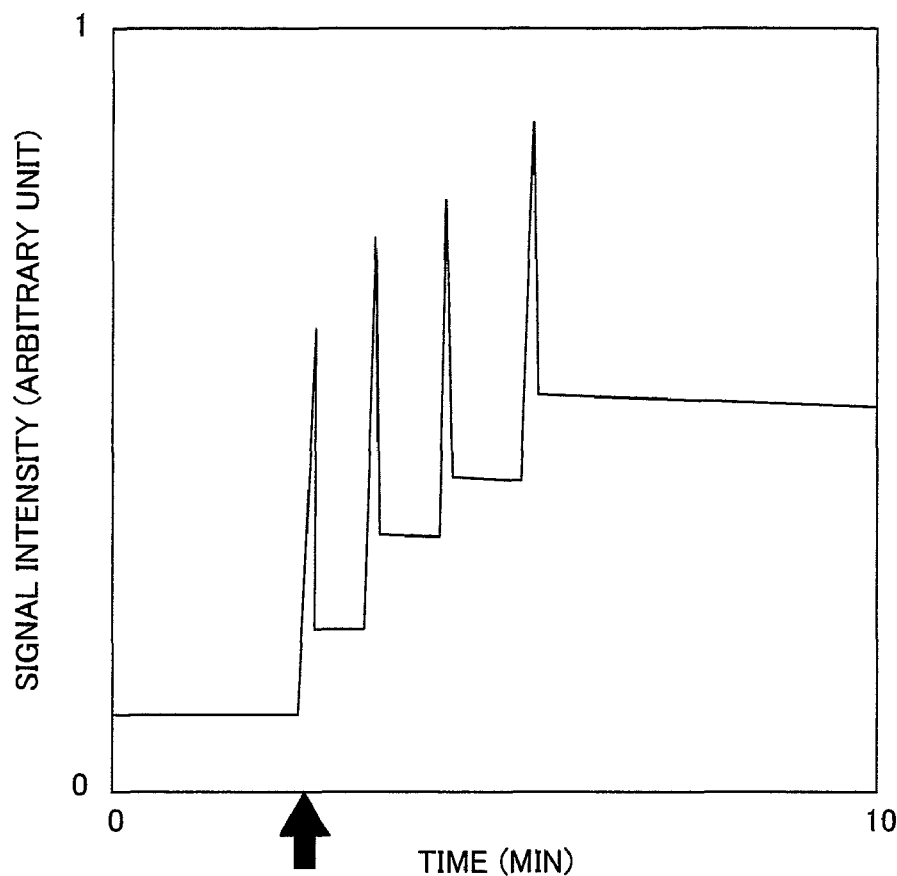
FIG. 6A and FIG. 6B are a luminescence measurement example and an outlines drawing of liquid feeding timing of a chemiluminescence reagent in the embodiment of the present invention.
Figure 6B:
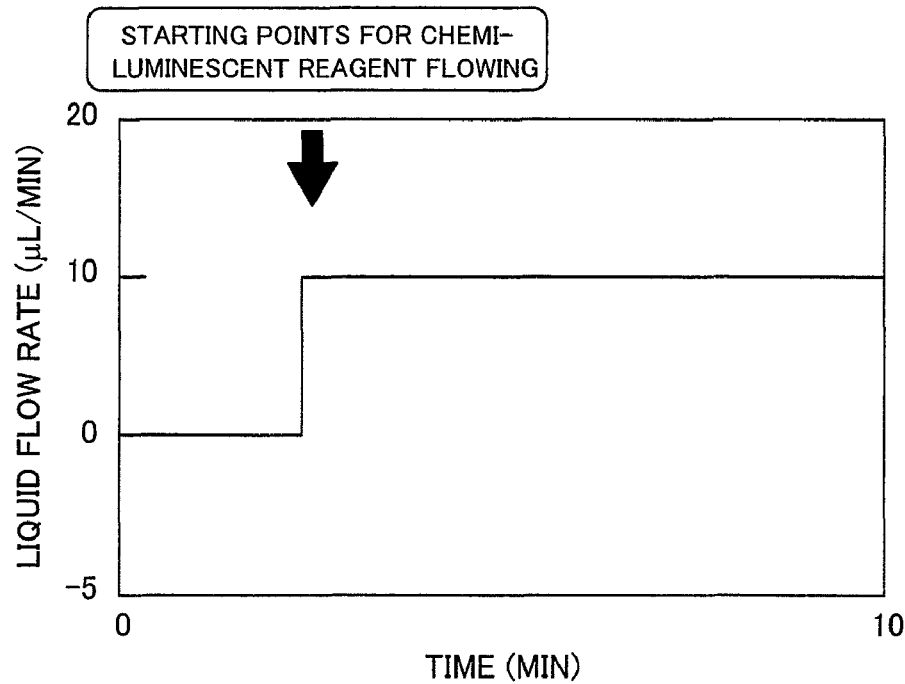

FIG. 6A is a schematic diagram of a luminescence measurement result example in the second embodiment and FIG. 6B is an outline of timing of chemiluminescence reagent feeding and the amount of liquid fed. A reaction similar to that in the first embodiment is caused similarly, but in the present embodiment, the sample solution contains, for example, α-fetoproteins, CA19-9, CEA, and PSA and detection thereof is intended. A solution containing HRP labeled antibodies for four substances was used as an HRP labeled antibody solution. Measurement starts at time 0 and, at this point, no chemiluminescence reagent has been fed and thus, no luminescence is measured. Signal intensity remains constant at a background level. A solution containing a chemiluminescence reagent is fed at the volume flow rate of 10 µL per minute in timing of the start of chemiluminescence reagent feeding and the feeding is continued. Like the first embodiment, a high peak of signal intensity due to luminescence is temporarily recorded. Thereafter, a total of four peaks are observed at intervals of about 1 minute. These peaks are each considered to be luminescence of bead vicinities where the anti-α-fetoprotein antibody, anti-C-19 antibody, anti-CEA antibody, and anti-PSA antibody are immobilized. Since the internal volume of piping between the beads arrays corresponding to the beads array 121 is set to be 10 µL, the time at which the solution containing the chemiluminescence reagent reaches each beads array can be estimated from the flow rate thereof and here, it is possible to interpret that four peaks are observed at intervals of about 1 minute because the time at which the solution reaches each beads array is shifted by about 1 minute for each beads array. By measuring luminescence while the chemiluminescence reagent being fed, as described above, there is an effect of being able to achieve detection of multiple items easily at a lower cost with the use of one optical detector and the apparatus configuration in which the optical detector is not moved.

Figure 7:
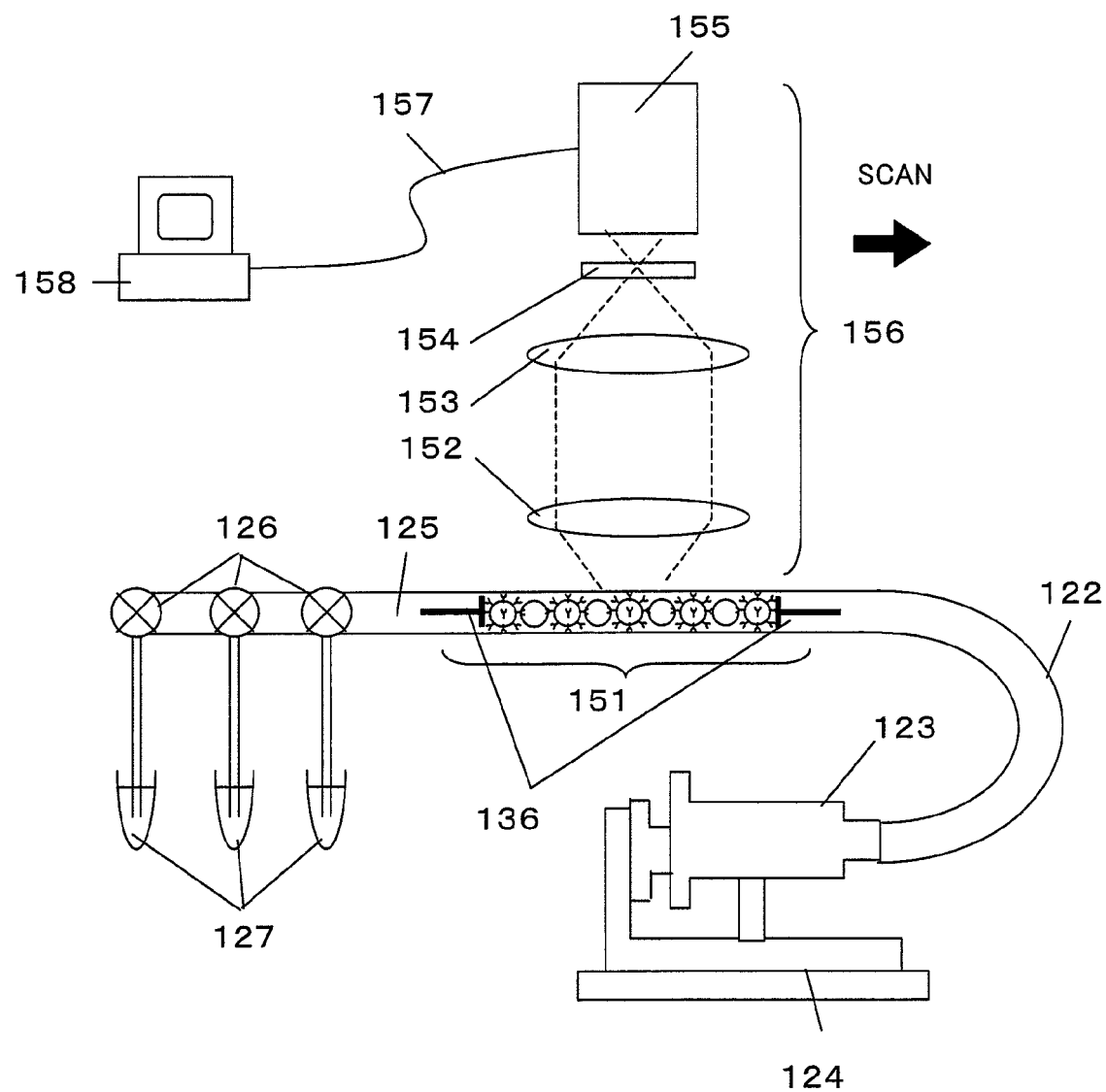
FIG. 7 is a schematic diagram of an apparatus in an embodiment of the present invention.

FIG. 7 shows an apparatus outline in a third embodiment. This is a system in which multiple items are detected by optical system scanning. A liquid feeding system similar to that in the first embodiment is connected to a beads array 151 in which probe immobilized beads and probe non-immobilized beads are alternately arranged for multiple items. One end of the beads array 151 is connected to the syringe 123 provided for the syringe pump 124 through the capillary 122.

The capillary 125, which is connected to the containers 127 via the valves 126, is provided on the other end of the beads array 151. Each of the containers 127 is accessed by operating the valve 126. Luminescence from a plurality of beads in the beads array 151 is separately measured by scanning with an optical system 156. The optical system 156 moves relative to the beads array 151. An objective lens 152 whose focal length is 9 mm and numerical aperture is 0.46, for example, is used and an imaging lens 153 whose focal length is 180 mm, for example, is used. The magnification in this case is 20 times, which is calculated as a ratio of focal lengths. A slit 154 is placed in an image plane set by the objective lens 152 and the imaging lens 153. A bead of 100 μm in the beads array 151, for example, will be an image of 2 mm in this virtual image plane. The slit 154 is used to cut out beads images and has a rectangular shape having a longitudinal direction in a direction substantially perpendicular to the longitudinal direction of the beads array 151. The slit width hereinafter will be described, instead of an actual size of the slit width, as a value multiplied by an inverse ratio of the magnification. For example, the slit width 20 μm is a slit width dividing a bead image of originally 100 μm into five in the horizontal direction. A PMT 155 is placed immediately behind the slit 154 to receive all amounts of light that has passed through the slit 154. Here, an example in which the receiving plane uses PMT whose diameter is 8 mm is shown. The PMT 155 is connected to a personal computer 158 as a data processing apparatus through a line 157. With this configuration, luminescence from the beads array 151 collected by the optical system 156 is guided to the PMT 155 before a signal is output from the personal computer 158.

Figure 8A:
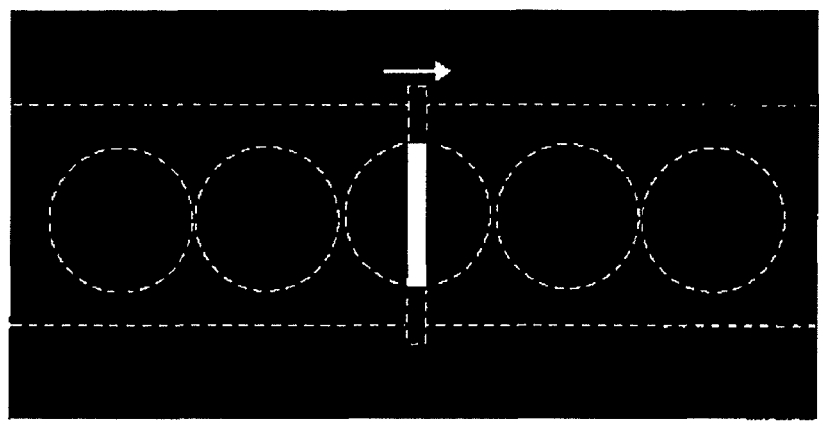
FIG. 8A and FIG. 8B are relational schematic diagrams between optical system scanning and data in the embodiment of the present invention.
Figure 8B:
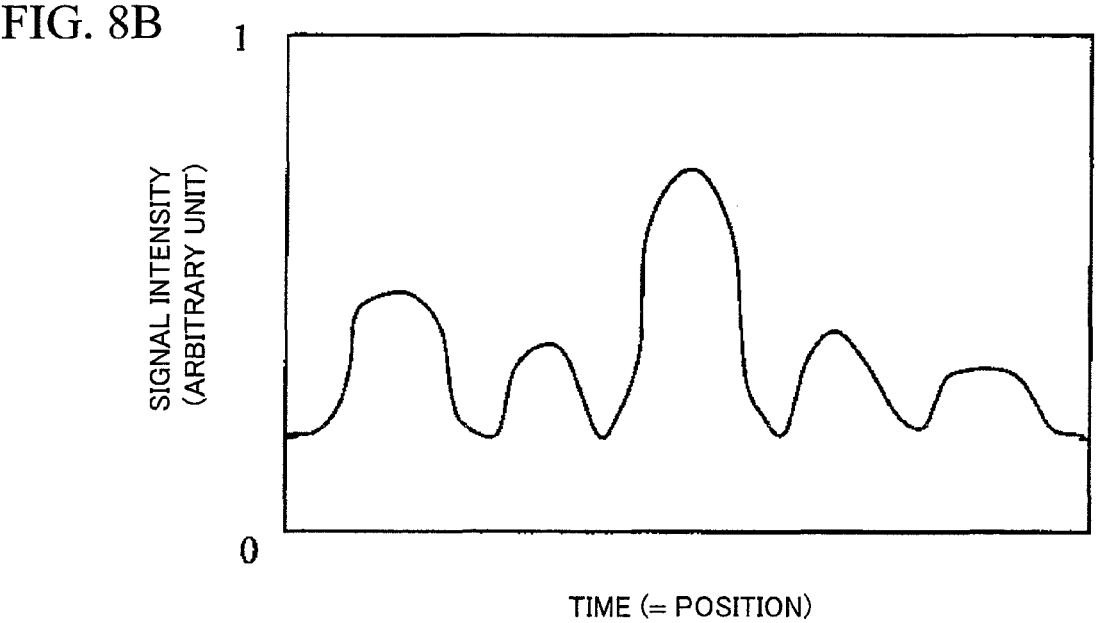

FIG. 8A and FIG. 8B show an outline of relationships between scanning by the optical system and data obtained in the third embodiment. FIG. 8A is a conceptual diagram showing relationships between a virtual beads array and a slit in the image plane. An example in which the slit width is set to 10 μm while the bead diameter is 100 μm is shown. Luminescence corresponding to a portion (white portion in FIG. 8A) cut out by the rectangular slit from a bead image is measured by the PMT. FIG. 8B, which shows conceptually that the elapsed time of scanning corresponds to the bead arrangement position, is a diagram showing that the bead position and luminescent intensity are associated. With an optical system including a slit that scans a beads array in the longitudinal direction, luminescence which has passed through the slit from beads of a beads array is measured as waveforms having position resolution. Higher signal intensity is obtained by broadening the slit width because the amount of light transmitted increases, but precise measurement is made more difficult because luminescence from each bead overlaps with each other. Moreover, if the scanning speed is too fast, waveforms is affected by the measuring band of the PMT, making waveforms dull. More specifically, if a reciprocal (expressible in seconds) of the measuring band of the PMT is equal to or longer than the scanning time for each bead, after receiving luminescence from some specific bead, a signal thereof extends over a time equal to or longer than needed for scanning the bead, making it difficult to distinguish beads. Thus, it is desirable to set the scanning speed in a range where the reciprocal of the measuring band is sufficiently smaller than the scanning time for each bead.

Figure 9A:
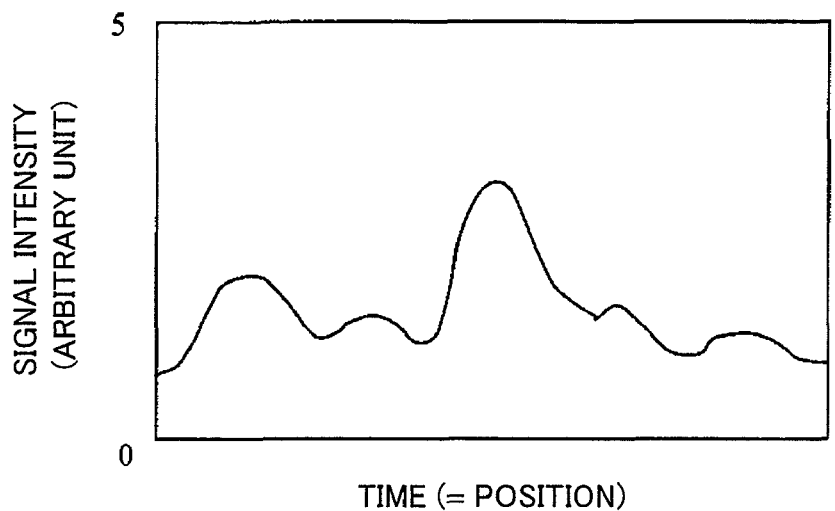
FIG. 9A, FIG. 9B and FIG. 9C are relational schematic diagrams between slit widths and signal waveforms in the embodiment of the present invention.
Figure 9B:
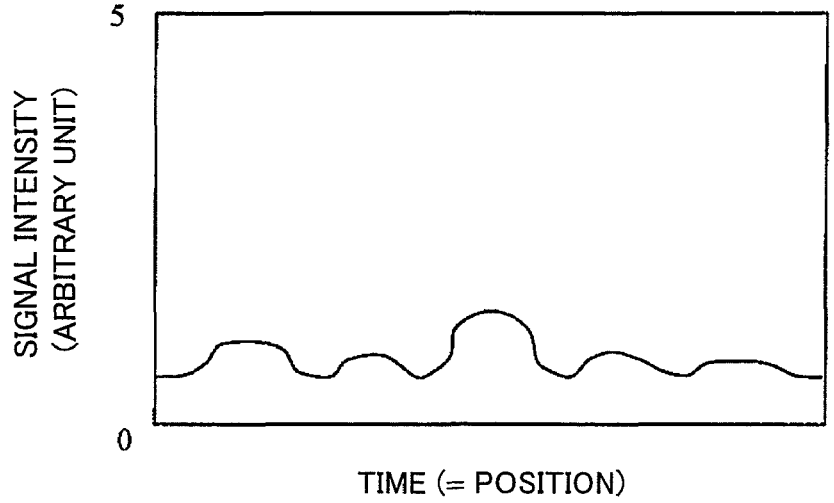
Figure 9C:
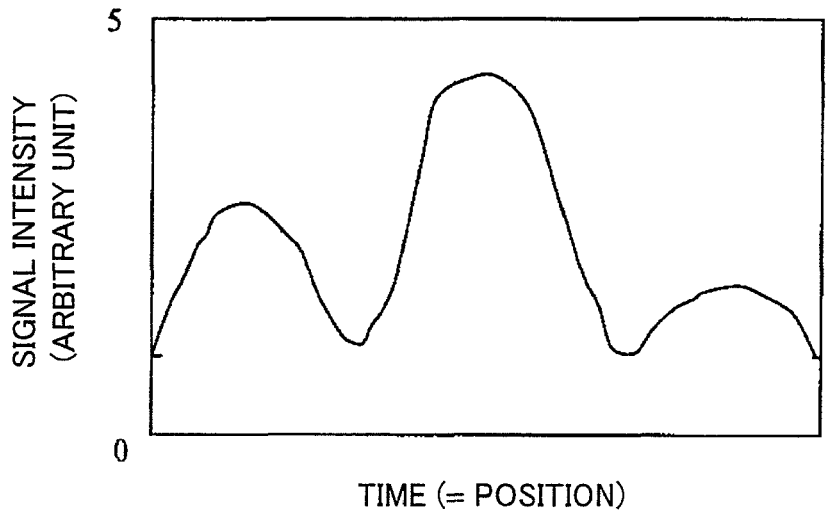

FIG. 9A, FIG. 9B and FIG. 9C schematically show relationships between the slit width and signal waveforms in the third embodiment. 5 seconds was set, for example, as the scanning time for each bead. If the measuring band of an apparatus shown in the third embodiment is about 2.5 Hz, this is an example in which waveforms are made dull only slightly by the band. The beads array is scanned by an optical system for measurement simultaneously while a reagent for a luminescent reaction is being flown into the beads array. FIG. 9A shows a case in which the slit width is 50 μm (about 50% of the bead diameter). In this case, the slit width is comparatively large and thus, a large signal is obtained. On the other hand, since luminescence from adjacent beads are also collected while bead edges are scanned by the slit, luminescence from each bead tends to be indiscernible. FIG. 9B shows a case in which the slit width is 10 μm (about 10% of the bead diameter). Luminescence from each bead can now be clearly distinguished, but sensitivity tends to decline because the slit width has been made smaller and thus signal intensity becomes lower. FIG. 9C shows a case in which the slit width is increased to 80 μm (about 80% of the bead diameter) and also a bead to be detected for luminescence is arranged alternately in an arrangement of a plurality of beads. From what has been described above, by placing at least one bead not to be used for measurement between beads to be measured, it becomes possible to increase the distance between beads to be detected and make clear separation of beads. By further increasing the slit width, in addition to the above beads arrangement, signal intensity can be increased. That is, there is an effect that, as a result, highly sensitive and high-resolution measurement can be performed.

Figure 10:
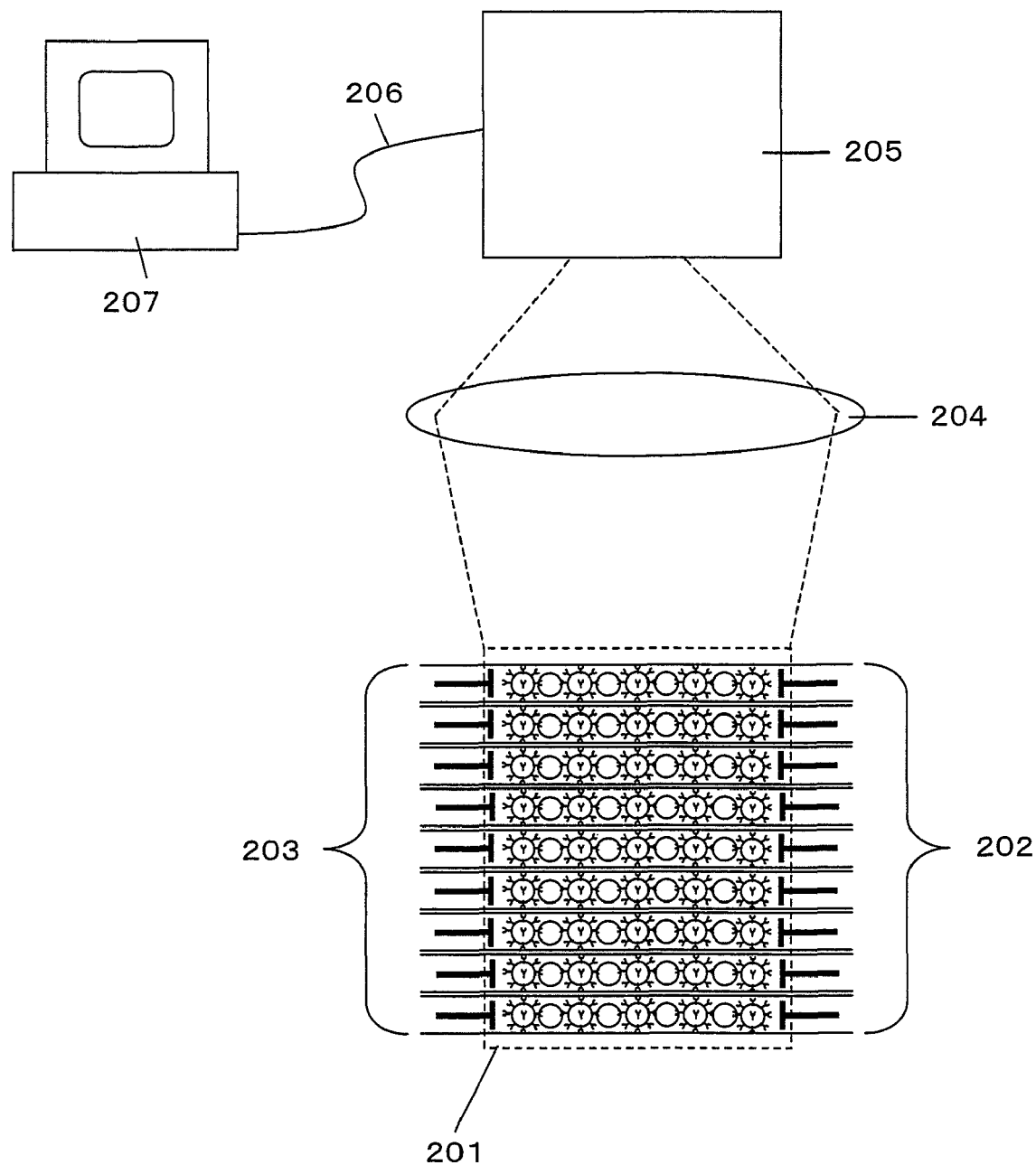
FIG. 10 is a schematic diagram of an apparatus in an embodiment of the present invention.

FIG. 10 shows an apparatus outline in a fourth embodiment. In contrast to the first to third embodiments, the optical system uses a CCD camera and thus can make measurements of many beads arrays at a time. Here, a beads array in which a probe immobilized bead for multiple items and a probe non-immobilized bead or light blocking bead are arranged alternately can be used. A liquid feeding system 202, and a solution holding part (not shown) and connection switching part 203 are connected to both sides of a beads array group 201 that consists of bundled beads arrays. The liquid feeding system is a part having a function to feed a solution to each beads array, and a system in which syringe are utilized and they are connected to their respective beads arrays, as shown in FIG. 3, or a system using a pump can be applied. The solution holding part and connection switching part 203 are a container part into which a reaction solution or a cleansing solution is poured and a part having a function to switch the solution respectively, and a system in which containers are arranged in parallel and a valve is connected to each container, as shown in FIG. 3, can be applied. The liquid feeding system 202, and the solution holding part and connection switching part 203 each have a function to pour a solution containing a reagent for a luminescent reaction into each beads array in the beads array group 201. The beads array group 201 is measured by a CCD camera 205 via a camera lens 204. The cameral lens 204 whose F value is 0.95 and focal length is 50 mm, for example, is used, whose image magnification is set to be an equimultiple. A bead of 100 μm in the beads array is projected onto a photon sensitive area of the CCD camera 205 as an image of the size of 100 μm. The CCD camera 205 is connected to a personal computer 207, which is a data processing apparatus, through a line 206, and an image obtained by the CCD camera 205 is processed by the personal computer 207 before being displayed. The CCD camera used here may be any camera.

Figure 11A:
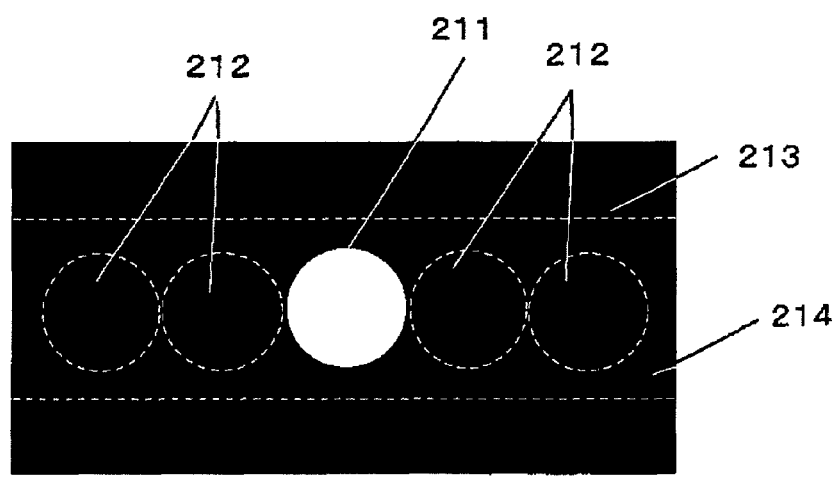
FIG. 11A and FIG. 11B are schematic diagrams of crosstalk of luminescence in the embodiment of the present invention.
Figure 11B:
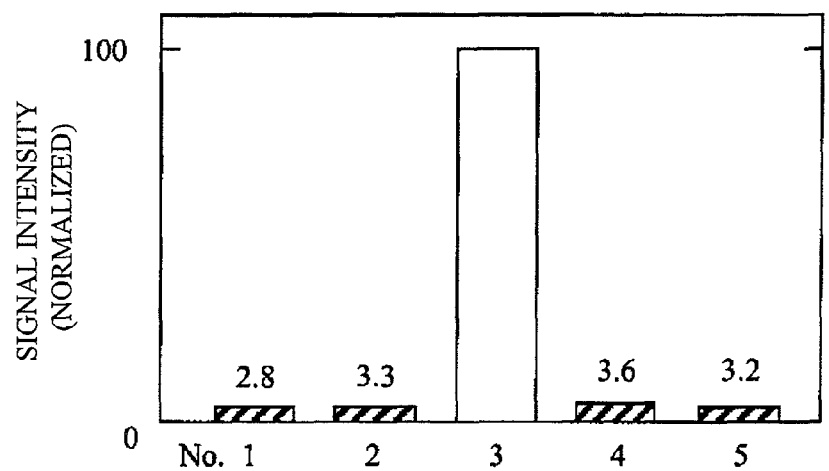

FIG. 11A and FIG. 11B are diagrams exemplifying crosstalk of luminescence from beads in the fourth embodiment. FIG. 11A is an enlarged schematic diagram of part of an image and FIG. 11B is a graph showing luminescent intensity observed for each bead after normalization. The measuring time was temporarily set to 5 minutes. What is shown in FIG. 11A is an example of polystyrene (PS) beads of 100 μm. This is a case in which beads 212 (Nos. 1, 2, 4, and 5) from which no luminescence is expected are arranged on both sides of a luminescent bead 211 (No. 3). The beads 211 and 212 are contained in a capillary 213 through whose space an aqueous solution 214 containing a chemiluminescence reagent is flowing. The aqueous solution 214 containing a chemiluminescence reagent is fed from the left side of FIG. 11A. FIG. 11B compares light intensity after normalizing it so that luminescent intensity of the luminescent bead 211 is equal to 100. As is evident from the graph, light from beads that should not be luminescent is measured with intensity of about 3%. This is not desirable for precise measurement. Particularly for detection of multiple items by use of beads arranged as described above, in which detection a large difference in luminescent intensity is expected, a large difference arises for items in which luminescence is weak. The most influential factor for measurement of light from beads from which no luminescence is expected is a crosstalk phenomenon in which the beads 212 from which no luminescence is expected is irradiated with luminescence from the luminescent bead 211, resulting in measurement depending on scattering or refraction.

Figure 12A:
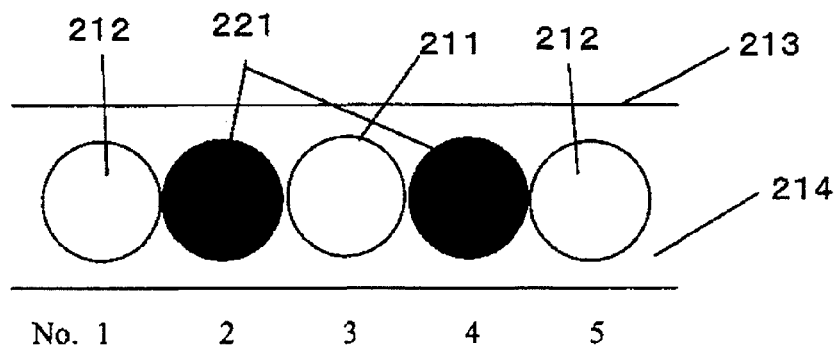
FIG. 12A, FIG. 12B and FIG. 12C are schematic diagrams of crosstalk of luminescence and an effect of light blocking beads in the embodiment of the present invention.
Figure 12B:
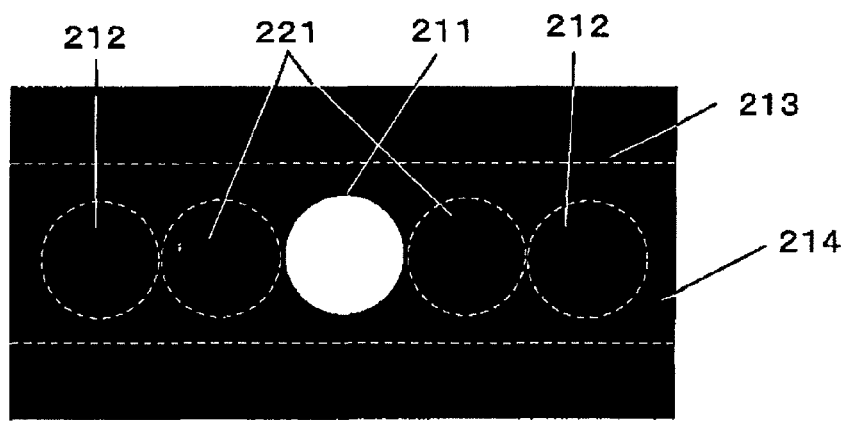
Figure 12C:
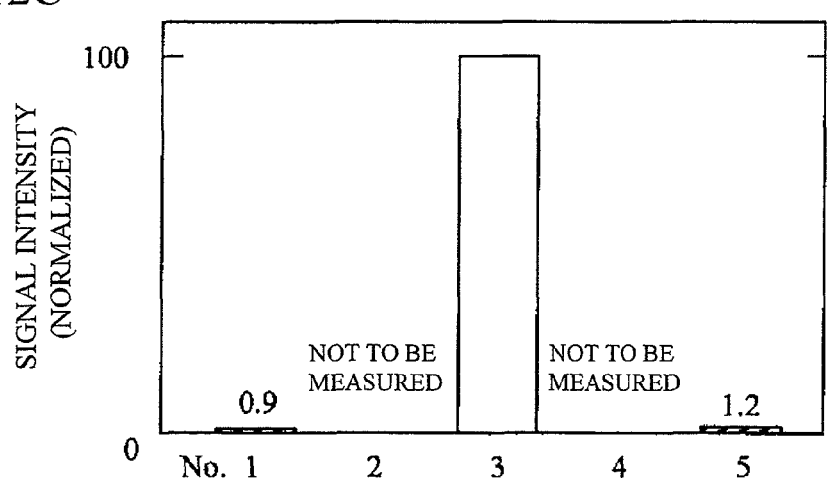

FIG. 12A, FIG. 12B and FIG. 12C are diagrams exemplifying a case in which light blocking beads are inserted against crosstalk of luminescence of beads in the fourth embodiment. FIG. 12A shows the configuration thereof. Light blocking beads 221 are inserted between the luminescent bead 211 and the non-luminescent beads 212. Here, beads prepared by mixing particles mixed with light blocking substance, for example, $MnO_2$ fine particles of 100 μm into polystyrene was used as the light blocking beads 221. Furthermore, any material showing light blocking properties including colored particles such as black, blue, and red, colored latex, metallic particles, and particles mixed with or comprising substance showing light blocking properties can be used. Particularly preferable are black particles with extremely low transmission of light regardless of material. That is, by wrapping black particles in polystyrene, a surface for the best immobilization can be provided while maintaining light blocking properties. FIG. 12B shows an enlarged schematic diagram of an image and FIG. 12C shows a graph showing luminescent intensity observed for each bead after normalization. The measuring time was temporarily set to 5 minutes. By inserting the light blocking beads 221, luminescent intensity of the bead at position of No. 1 is significantly reduced from 2.8% to 0.9% and that of the bead at position of No. 5 from 3.2% to 1.2%. The light blocking beads 221 have an effect of reducing the amount of crosstalk by blocking luminescence of the luminescent bead 211.

The luminescence wavelength is about 420 nm in luminol-based luminescence used in the present embodiment and any material blocking the wavelength as material properties of light blocking beads can be used. Plastic beads mixed with ferrite, those mixed with black pigment, and beads on which gold is evaporated can be considered. A system in which only one bead of 100 μm is inserted is considered here, but the present invention is not limited to this and a similar effect can be expected in a system in which some light blocking beads of 30 μm or less, for example, are inserted.

Figure 13A:
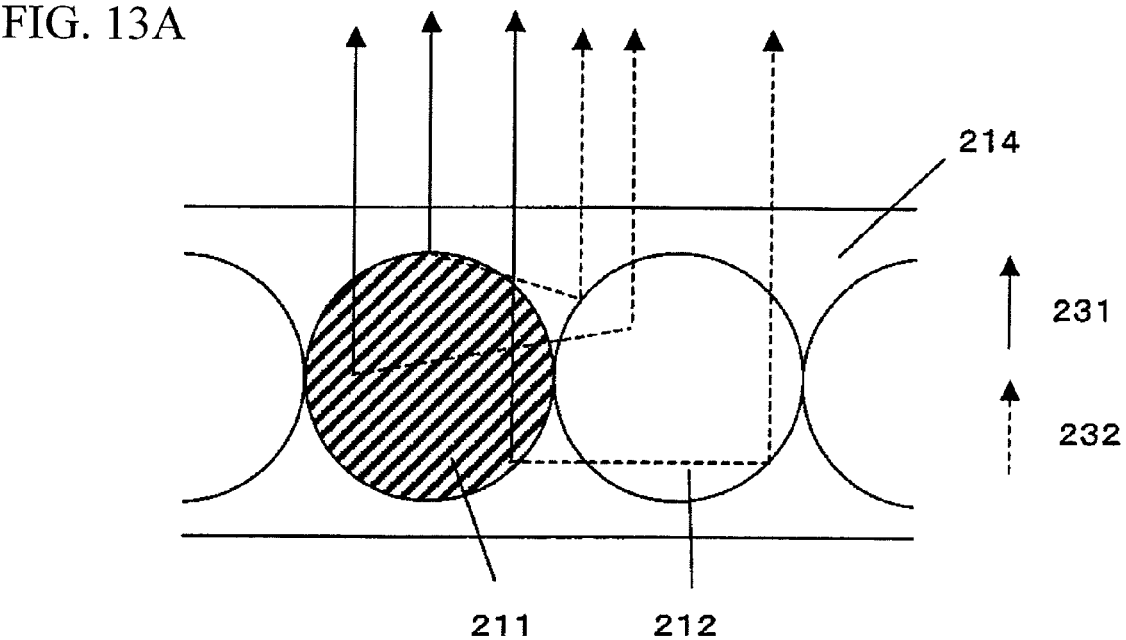
FIG. 13A and FIG. 13B are schematic diagrams of crosstalk of luminescence and an effect of adjusting a refractive index of a solution in the embodiment of the present invention.
Figure 13B:
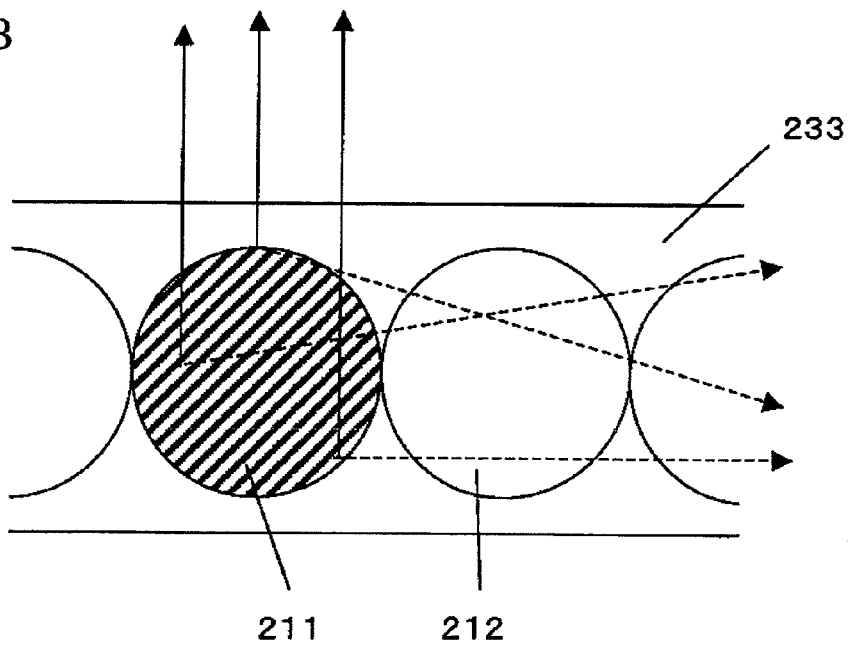

FIG. 13A and FIG. 13B are diagrams schematically showing an effect of adjusting the refractive index of a solution against crosstalk of luminescence from beads in the fourth embodiment. FIG. 13A is schematic diagram when no adjustment of the refractive index is made. Luminescence from the luminescent bead 211 is either a light beam 231 directed toward an optical system directly or a light beam 232 directed toward an adjacent bead. If, for example, the refractive index of an aqueous solution 214 containing a reagent for a luminescent reaction is around 1.33 and polystyrene, which is a material of the beads, is taken as an example, the refractive index thereof is 1.58. Thus, the light beam 232 directed toward the adjacent bead is subject to scattering or refraction on the surface of the bead 212 and consequently, redirected toward the optical system, to be observed, as a result, as crosstalk of the non-luminescent bead 212. FIG. 13B is a schematic diagram when adjustments of the refractive index are ideally made. If a solution 233 can be prepared as having the same refractive index as that of polystyrene, the light beam 232 directed toward the adjacent bead will not be subject to scattering or refraction on the surface of the bead 212. Thus, crosstalk caused by scattering or refraction can be reduced to 0. That is, crosstalk can be reduced by forming the solution and beads in such a way that the refractive index of the solution is close to that of beads. Adjustments of the refractive index are simpler in chemiluminescence using chemical excitation without using any enzyme because the organic solvent can be selected from a wider range of choice. While the above polystyrene has the refractive index of 1.58, if the material of beads has a lower refractive index, for example, glass with the refractive index of 1.47, the refractive index of the solution can be adjusted in a narrow range so that crosstalk can be prevented more easily.

Figure 14:
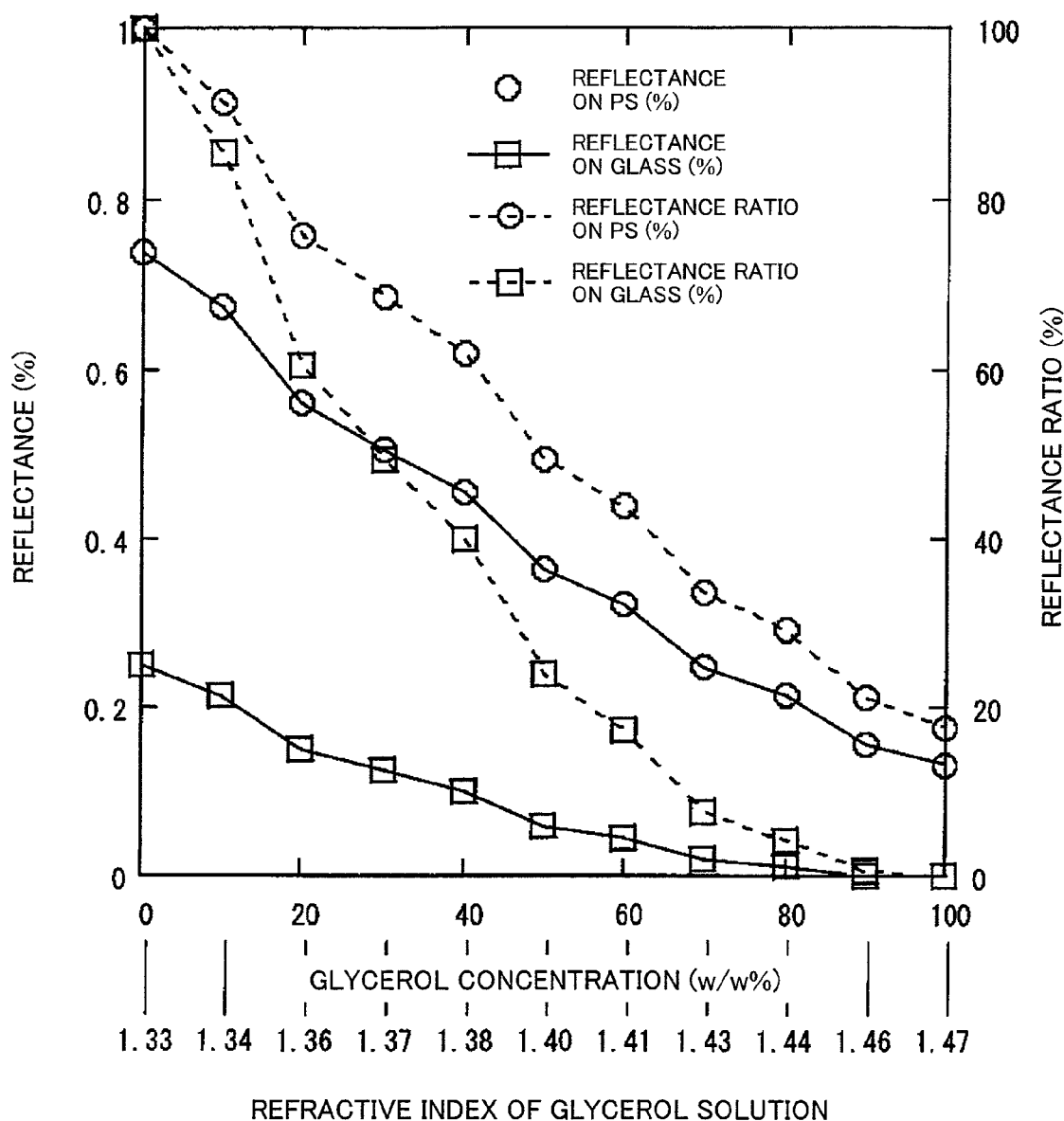
FIG. 14 is a graph diagram of reflectance after adjusting the refractive index of the solution in the embodiment of the present invention using glycerol.

FIG. 14 is a graph verifying an effect of adjusting the refractive index of a solution using glycerol against crosstalk of luminescence from beads in the fourth embodiment, from the standpoint of reflectance. Glycerol is known as a material that considerably changes the refractive index of an aqueous solution and only slightly affects an enzyme reaction. The refractive index of a glycerol aqueous solution increases from 1.33 to 1.47 as its concentration with respect to weight (percentage by weight) increases. Crosstalk has been evaluated by representing it by the reflectance of light in the vertical direction and the reflectance as a reflectance ratio has been calculated by setting the reflectance when the glycerol concentration is 0% as 100%, for the graph. When beads are made of polystyrene (PS), the reflectance of its aqueous solution is 0.74%. When the glycerol concentration increases, a difference of refractive indexes decreases and thus the reflectance also decreases. If, for example, the glycerol concentration is 50%, the reflectance ratio drops to 50%, bringing about a sufficient effect. The difference of refractive indexes at this time is 0.18. If the glycerol concentration exceeds 80%, viscosity enormously increases and thus, a problem may be caused in actually feeding the aqueous solution. That is, when beads are made of polystyrene, the glycerol concentration is preferably set between 50% and 80%. If beads are made of glass, the reflectance with respect to an aqueous solution is 0.25%, which is 1/3 of that when beads are made of polystyrene, and the reflectance ratio drops to 49%, which is below a half value, only by increasing the glycerol concentration to 30%. That is, when beads are made of glass, the glycerol concentration is preferably set between 30% and 80%. Considering modes of general beads used for beads arrays, from the above conditions, it is generally preferable to set the glycerol concentration between 30% and 80%. A case in which glycerol is used is shown, but the present invention is not limited to this and any solvent that changes the refractive index can also be used.

Suppose that the refractive index of a bead is nb and that of a solution is ns and that the reflectance is represented by a reflectance k at an interface in the vertical direction, we have a relation $k=(nb-ns)^2/(nb+ns)^2$. The glycerol range in a glycerol solution is preferably, as shown above, between 30% and 80%. It is also preferable that a difference between the refractive index of a bead and that of a solution is small for other solutions, but a difference of about 0.2 is considered to effectually achieve a sufficient effect from following considerations. Solving the above equation of reflectance with respect to the reflectance ns of a solution yields ns=nb*[(1+k)/(1−k)+ {(1+k)$^2$/(1−k)$^2$−1}]. nb can be set to 1.58 when the material of bead is polystyrene and nb can be set to 1.47 when the material of bead is glass. Considering the reflectance when the refractive index is not adjusted with respect to a chemiluminescence reagent as k0 and that a sufficient effect is achieved when the reflectance is halved, the value of 0.5×k0 can be substituted into k. The refractive indexes ns of the solution are calculated to be 1.40 and 1.37 when beads are made of polystyrene and glass respectively. Their respective differences from the refractive indexes of bead will be 0.18 and 0.10. Considering that the refractive index of resin is generally greater than that of glass and that resin other than polystyrene may be adopted, a sufficient effect can be achieved by setting the difference of refractive indexes to about 0.2 or less.

Figure 15A:
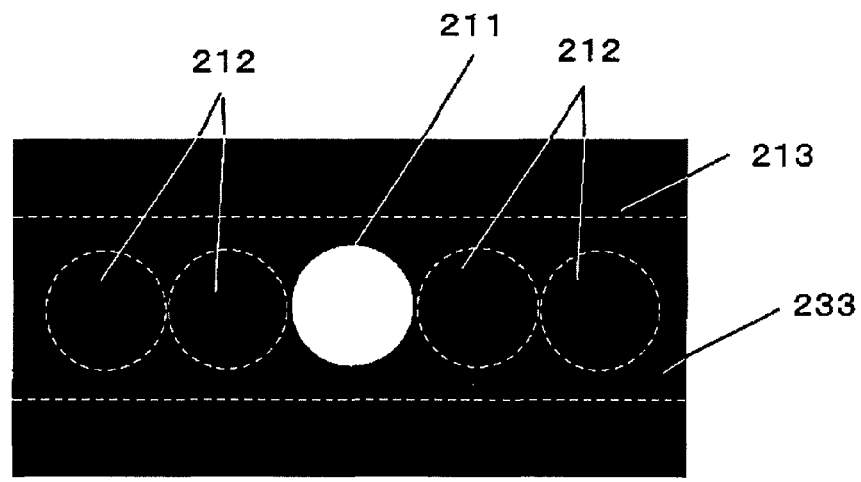
FIG. 15A and FIG. 15B are schematic diagrams of crosstalk of luminescence and an effect of a solution of glycerol 70% in the embodiment of the present invention.
Figure 15B:
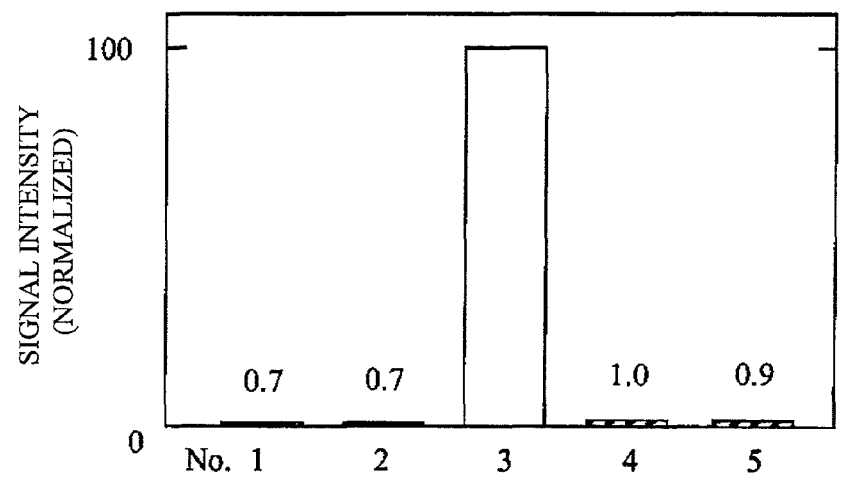

FIG. 15A and FIG. 15B are diagrams exemplifying a case in which the concentration of content glycerol in a solution containing a reagent for a luminescent reaction is adjusted to 70% against crosstalk of luminescence from beads in the fourth embodiment. The refractive index of the solution 233 at this time is 1.43. Other components are the same as those in FIG. 11A and FIG. 11B and polystyrene whose refractive index is 1.58 is used for beads. FIG. 15A shows an enlarged schematic diagram of an image and FIG. 15B shows a graph showing luminescent intensity observed for each bead after normalization. The measuring time was set to 5 minutes. By adjusting a solution of a reagent for a luminescent reaction to that of glycerol 70%, luminescence intensity of the non-luminescent bead 212 can be prevented from rising above 0.7% to 1.0% of the amount of luminescence of the bead 211 contributing to luminescence. This value is about ¼ of the value when the refractive index is not adjusted, achieving a substantial reduction. It is considered that, by bringing the refractive index of a solution closer to that of a bead, an effect of reducing the amount of crosstalk of the beads 212 from which no luminescence is expected is produced.

Beads arrays are used in the present embodiment, but the present invention is not limited to the use of beads arrays. If, in a device having a channel in which a probe for capturing a biochemical to be detected is immobilized on a solid phase, luminescence is detected by measuring vicinities of an area where the probe is immobilized, a problem of crosstalk generally arises and thus the present embodiment is effective.

Figure 16:
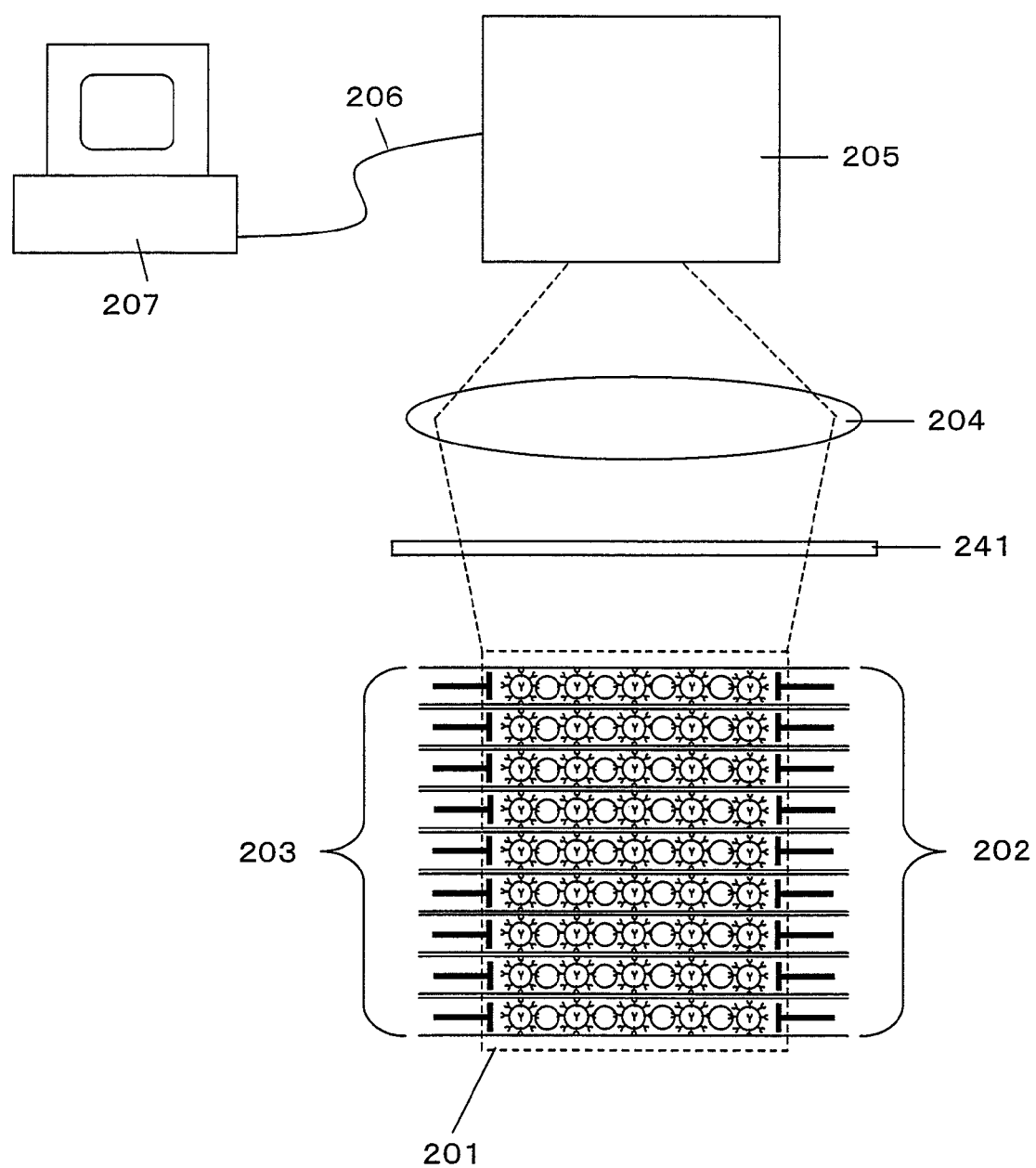
FIG. 16 is a schematic diagram of an apparatus in the embodiment of the present invention.

FIG. 16 shows an apparatus outline of the fourth embodiment related to reduction in crosstalk by using a polarizing plate. In addition to the apparatus configuration shown in FIG. 10, a polarizing plate 241 is inserted between the beads array group 201 and the CCD camera 205. While luminescence from the beads array group 201 is considered not to be polarized because the luminous substrate emits light in random directions, crosstalk reflected by adjacent beads is considered to be polarized because of a difference between the reflectance of s waves and that of p waves. Thus, by inserting the polarizing plate 241, a contribution from crosstalk can be made smaller. This method has an advantage over systems using light blocking fine particles or those of adjusting the refractive index of a solution described from FIG. 12A to FIG. 15B in that crosstalk can be reduced with a very simple configuration at a lower cost.

EXAMPLES

Example 1

Figure 17:
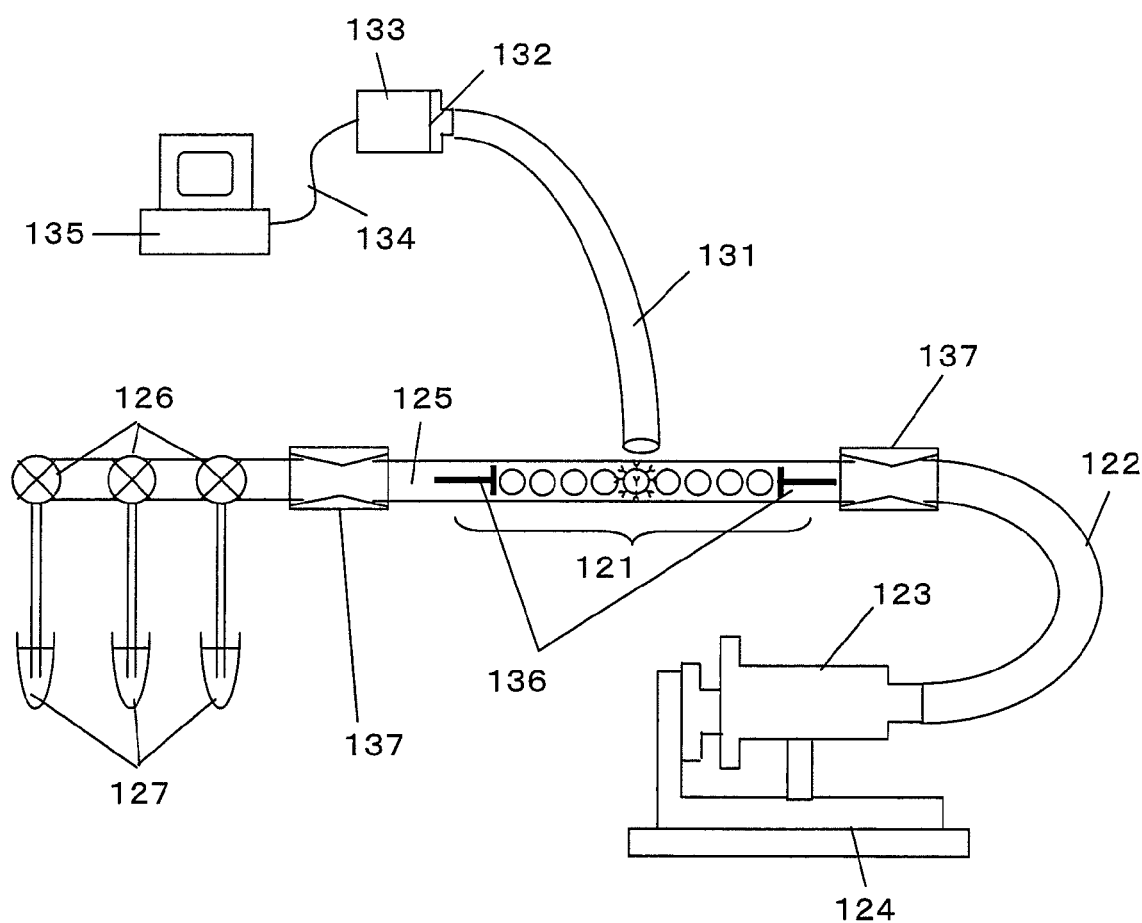
FIG. 17 is a schematic diagram of a laboratory apparatus of examples 1 and 2 of the present invention.

FIG. 17 shows an outline of the apparatus used for the experiment. Reactions were caused in accordance with the flow chart shown in FIG. 1.

Ten drops (about 1 mL) of suspension of polystyrene beads (manufactured by JSR, polystyrene standard particle DYNOSPHERES, model number: SS-922P) of 93 μm were taken by an Eppendorf tube of 1.5 mL and the suspension was separated by a compact desktop centrifuge (Chibitan of Millipore, manufactured by Tomy Seiko) into beads and a supernatant. After removing the supernatant using a pipette, 1 mL of 10 μg/mL anti-IgE antibody (manufactured by Bethyl, Goat Anti-Human IgE-affinity Purified, model number: A80-108A) prepared with a carbonate buffer solution (NaHCO$_3$: 3.0 g, Na$_2$CO$_3$: 1.5 g, water: 1 L, pH: 9.6) was added to the beads before they were left alone for one night for immobilization. Subsequently, the supernatant was removed, the carbonate buffer solution was added and stirred, and again the desktop centrifuge was used for separation into a supernatant and beads before the supernatant was removed. This cleansing operation was repeated three or four times. Block Ace (Trademark) (distributed by Dainippon Sumitomo Pharma, manufactured by Snow Brand Milk Products) was used for blocking for one hour.

Beads (hereinafter called blank beads) for which only blocking processing was performed with Block Ace (Trademark) and on which no anti-IgE antibody was immobilized, were separately prepared.

A fused silica capillary (manufactured by GL Science) whose outside diameter is 375 μm and inside diameter is 150 μm was cut to a 10-cm piece, an observation window was provided by separating polyimide on the surface in a center portion thereof by combustion method, and 10 blank beads, 1 anti-IgE antibody immobilized bead, and 10 blank beads were arranged therein in this order. Both ends were fixed by a SUS304 stainless wire (manufactured by Nilako, model number: 751107) with a diameter of 50 μm. This device was used to use an apparatus in FIG. 17 to cause reactions and detect them. An inner seal connector (manufactured by GL Science, applicable inside diameter: 250 to 530 μm) was used for connecting each capillary.

First, 50 μL of Block Ace (Trademark) was fed reciprocatingly (10 reciprocations) at the flow rate of 100 μL/min to cause reactions for 10 minutes (blocking of the channel).

Next, 50 μL of 1 ng/mL IgE (manufactured by Bethyl, Human IgE Calibrator, model number: RC80-108) diluted by a phosphate buffer solution (manufactured by Wako Pure Chemical Industries, phosphate buffered saline powder (NaH$_2$PO$_4$: 0.35 g, Na$_2$HPO$_4$: 1.28 g, NaCl: 8 g in 1 L), pH: 7.4, hereinafter abbreviated as PBS) was fed reciprocatingly (20 reciprocations) at the flow rate of 100 μL/min to cause reactions for 20 minutes.

The PBS was swept along in one direction at the flow rate of 100 μL/min for cleansing for 4 minutes. Fifty μL of 1000 ng/mL HRP labeled anti-IgE antibody (manufactured by Bethyl, Goat Anti-Human IgE-HRP Conjugate) diluted by the PBS was fed reciprocatingly (20 reciprocations) at the flow rate of 100 μL/min to cause reactions for 20 minutes. The PBS was swept along in one direction at the flow rate of 100 μL/min for cleansing for 4 minutes.

Figure 18:
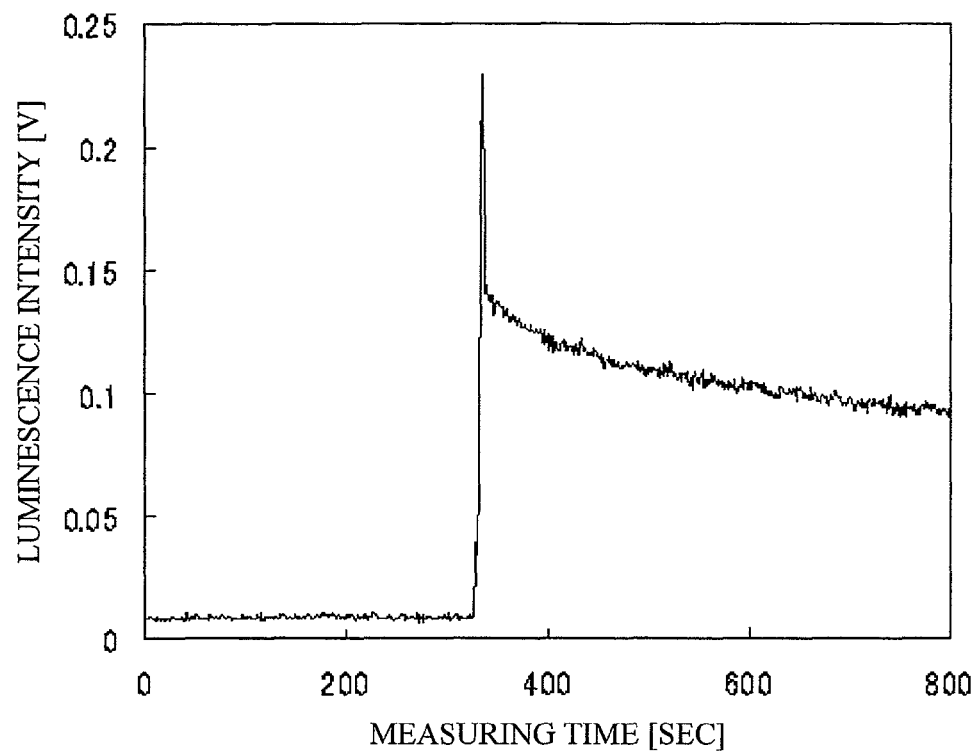
FIG. 18 is a diagram showing a measurement result of the example 1 of the present invention.

FIG. 18 shows a result of luminescence measurement using SuperSignal (Registered Trademark) WestFemto (manufactured by PIERCE) as a luminous substrate of HRP. When the above luminous substrate was added as a reagent for a luminescent reaction (near 320 sec), a peak resulting from luminescence was obtained. When integrated for 100 seconds, the resultant value was 5.5. A similar experiment for 0 ng/mL IgE (without IgE) yielded a value of 2.3.

Example 2

FIG. 17 shows an outline of the apparatus used for the experiment. Reactions were caused in accordance with the flow chart shown in FIG. 1.

Ten drops (about 1 mL) of suspension of polystyrene beads (manufactured by JSR, polystyrene standard particle DYNOSPHERES, model number: SS-922P) of 93 µm were taken by an Eppendorf tube of 1.5 mL and the suspension was separated by the compact desktop centrifuge (Chibitan of Millipore, manufactured by Tomy Seiko) into beads and a supernatant. After removing the supernatant using a pipette, 1 mL of a solution from cedar pollen extract prepared with PBS to 50 µg/mL was added to the beads before they were left alone for one night for immobilization of cedar pollen extracted antigens. Subsequently, the supernatant was removed, the carbonate buffer solution was added and stirred, and again the desktop centrifuge was used for separation into a supernatant and beads before the supernatant was removed. This operation was repeated three or four times. One mL of Block Ace (Trademark) (distributed by Dainippon Sumitomo Pharma, manufactured by Snow Brand Milk Products) was added for blocking for one hour.

Beads (hereinafter called blank beads) for which only blocking processing was performed with Block Ace (Trademark) and on which no cedar pollen extracted antigen was immobilized, were separately prepared.

A chip with grooves of inside dimensions 110 µm×110 µm in polymethyl methacrylate of the size 3.0 cm×4.0 cm×0.15 cm was used as a device. An open portion of the chip was filled up by laminating films of the thickness 50 µm made of the same material. Ten blank beads, 1 cedar antigen immobilized bead, and 10 blank beads were arranged in the chip in this order. One end of the chip is provided with a dam structure to prevent beads from flowing out and the other end has a taper structure and beads can be prevented from flowing out by inserting a fused silica capillary (manufactured by GL Science) whose outside diameter is 375 µm and inside diameter is 50 µm. An inner seal connector (manufactured by GL Science, applicable inside diameter: 250 to 530 µm) was used for connecting each capillary.

First, 50 µL of Block Ace (Trademark) was fed reciprocatingly (10 reciprocations) at the flow rate of 100 µL/min to cause reactions for 10 minutes (blocking of the channel).

Fifty µL of 100 ng/mL monoclonal mouse anti-cryj1 antigen (manufactured by Hayashibara Biochemical Labs., AB-Cedar Pollen Allergen Cryj1, (026) (mo) (M), Affin) prepared with the PBS was fed reciprocatingly (20 reciprocations) at the flow rate of 100 µL/min to cause reactions for 20 minutes. The PBS was swept along in one direction at the flow rate of 100 µL/min for cleansing for 4 minutes. Fifty µL of 1000 ng/mL HRP labeled anti-mouse IgG antibody (manufactured by Dako, Anti-Mouse Immunoglobulins/HRP, model number: P0447) prepared with the PBS was fed reciprocatingly (20 reciprocations) at the flow rate of 100 µL/min to cause reactions for 20 minutes. The PBS was swept along in one direction at the flow rate of 100 µL/min for cleansing for 4 minutes.

Figure 19:
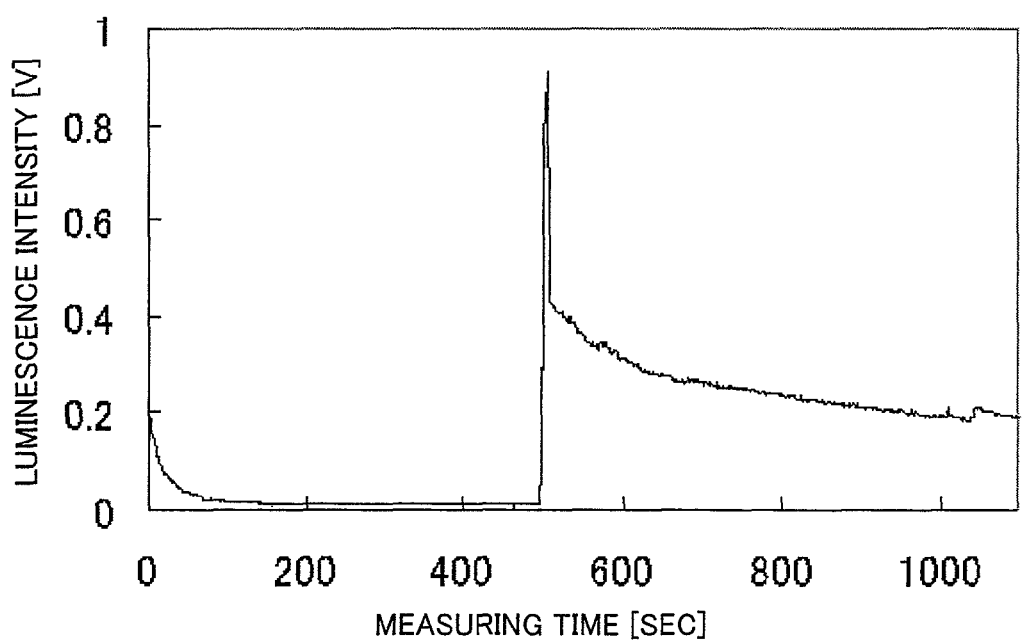
FIG. 19 is a diagram showing a measurement result of the example 2 of the present invention.

In FIG. 19, a peak was obtained when feeding of a solution was started using SuperSignal (Registered Trademark) WestFemto (manufactured by PIERCE) as a reagent for a luminescent reaction (near 500 sec). When integrated for 100 seconds, the resultant value was 16.2.

Example 3

Figure 20:
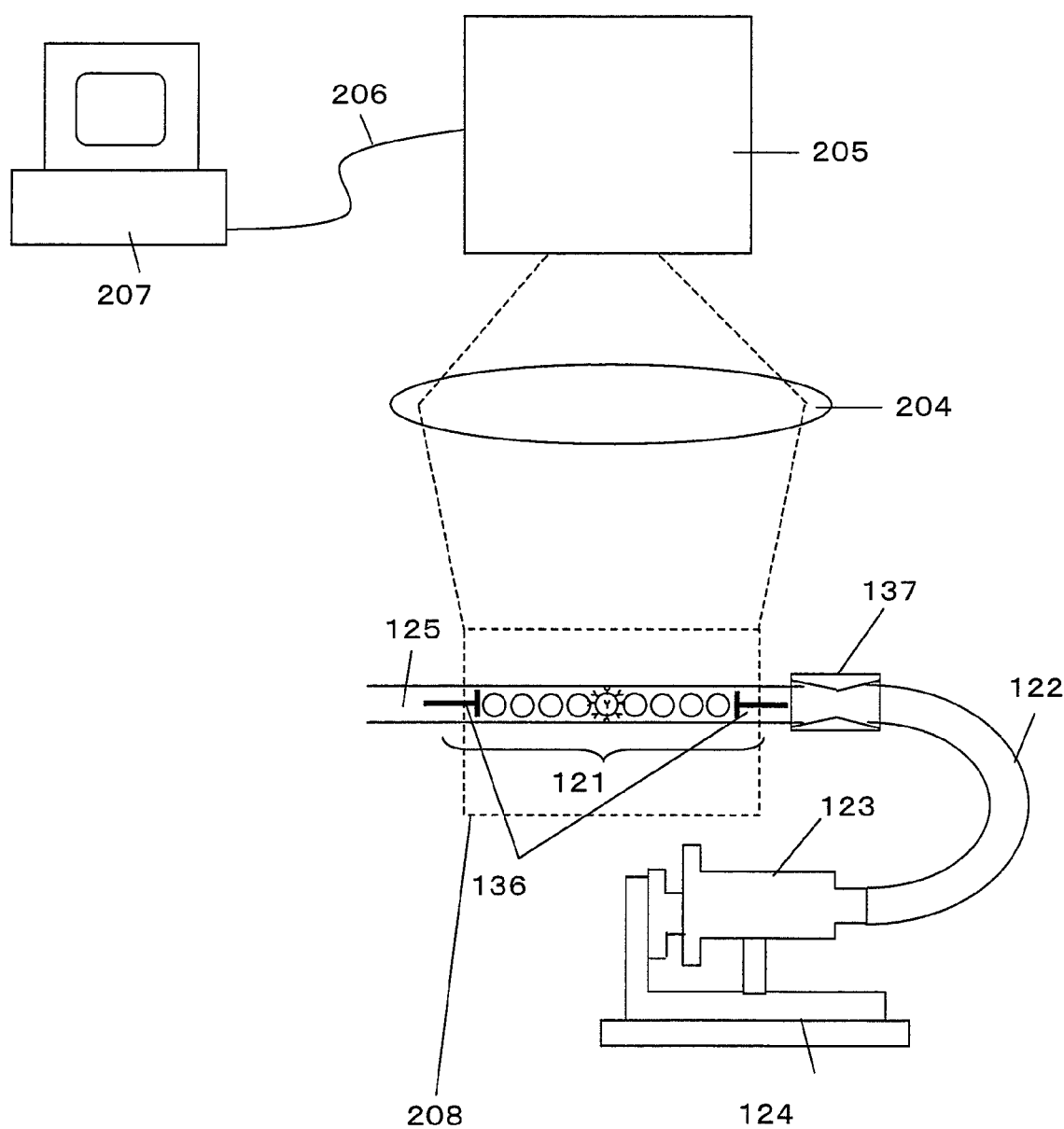
FIG. 20 is a schematic diagram of a laboratory apparatus of an example 3 of the present invention.

FIG. 20 shows an outline of the apparatus used for the experiment. Ten µg/mL HRP labeled anti-Aldolase antibody (manufactured by ROCKLAND, Anti-Aldolase, Rabbit Muscle, Goat-Poly, HRP, model number: 200-1341) prepared with the PBS was put in a refrigerator throughout the night so as to be immobilized on PS beads (manufactured by Polyscience, range of particle diameter: 250 to 300 µm) of 250 µm.

The above bead was sandwiched by several black beads (manufactured by DukeScience, particle diameter: 50 µm, model number: BK050T) on both sides and further 250 µm PS beads on which nothing was immobilized were arranged on both sides inside fused silica (manufactured by GL Science) whose outside diameter is 450 µm and inside diameter is 320 µm.

Both ends were fixed by a SUS304 stainless wire (manufactured by Nilaco, model number: 751107) with a diameter of 50 µm.

Figure 21:
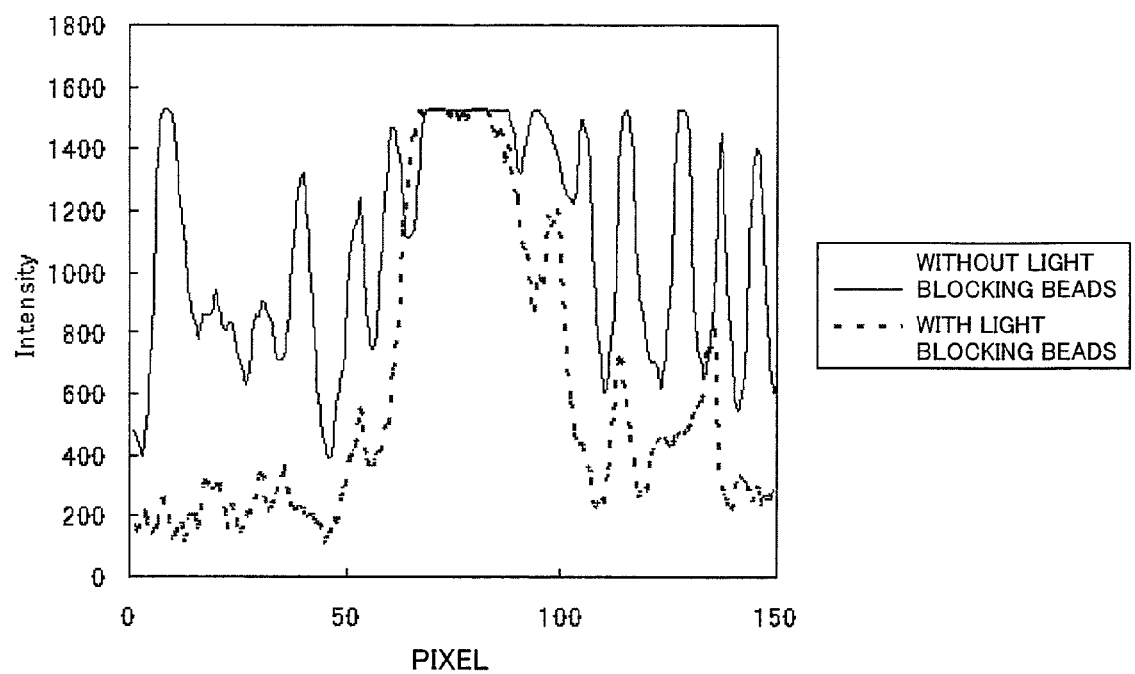
FIG. 21 is a diagram showing a measurement result of the example 3 of the present invention.

A luminous substrate of HRP, SuperSignal (Registered Trademark) WestFemto (manufactured by PIERCE), was used as a reagent for a luminescent reaction and the luminous substrate was set inside a syringe pump before feeding a solution to the beads array. A result of integration for 5 minutes after starting to feed the solution was obtained as a line profile on the beads array device, and FIG. 21 shows a graph showing intensity with respect to pixels.

For comparison, a result of blank beads sandwiched by HRP labeled anti-Aldolase antibody immobilized beads is shown.

As a result, when a bead to be detected is sandwiched by light blocking beads, leakage of light to adjacent beads could be prevented.

The invention claimed is:

1. An analysis method of a biochemical, comprising:
    a step of supplying a liquid containing a labeled substance to be detected or an unlabeled substance to be detected to a channel containing a solid phase to which a probe is bonded at least in part thereof;
    a step of causing said probe to capture said labeled substance to be detected or a step of causing the probe to capture the unlabeled substance to be detected and labeling the unlabeled substance;
    a step of supplying a reagent for a luminescent reaction to said channel by means of a liquid flow; and
    a step of optically detecting a vicinity of a region where the reagent for said luminescent reaction and said labeling have reacted,
    wherein said solid phase is a plurality of particles, said plurality of particles consist of light blocking particles and particles to be detected on which said probe is immobilized, and at least one light blocking particle is arranged between said particles to be detected.

2. The analysis method according to claim 1, wherein in the step of causing said probe to capture said labeled substance to be detected or the step of causing the probe to capture the unlabeled substance to be detected and labeling the unlabeled substance, a liquid containing the labeled substance to be detected or the unlabeled substance to be detected is supplied by means of reciprocating liquid feeding.

3. The analysis method according to claim 1, wherein said labeling is an enzyme and the reagent for said luminescent reaction contains a substrate corresponding to the enzyme used.

4. The analysis method according to claim 3, wherein said enzyme is peroxidase, alkaline phosphatase, glucose oxidase, β-D-galactosidase, glucose-6-phosphate dehydrogenase, invertase, adenosine triphosphate (hereinafter referred to as ATP) ase, luciferase, or aequorin, and said substrate is luminol, dioxetane, peroxyoxalate, glucose, β-D-galactosyl, glucose-6-phosphate, lucigenin, ascorbic acid phosphate, adenosine triphosphate, luciferin, or derivatives thereof, or calcium ions.

5. The analysis method according to claim 4, wherein the reagent for said luminescent reaction further includes an oxidizing agent or oxygenated additive.

6. The analysis method according to claim 3, wherein said enzyme is peroxidase, said substrate is luminol or a luminol derivative, and the reagent for said luminescent reaction further includes an oxidizing agent or oxygenated additive.

7. The analysis method according to claim 6, wherein said oxidizing agent is hydrogen peroxide or peracid including alkyl hydroperoxide.

8. The analysis method according to claim 3, wherein the reagent for said luminescent reaction further includes an enhancer.

9. The analysis method according to claim 1, wherein said vicinity is a vicinity of said plurality of particles.

10. The analysis method according to claim 1, wherein said step of detection and the step of supplying the reagent for said luminescent reaction to the channel by means of the liquid flow are performed simultaneously.

11. The analysis method according to claim 9, wherein a difference between a refractive index of a solution containing the reagent for said luminescent reaction supplied to said channel and a refractive index of said particles is about 0.2 or less.

12. The analysis method according to claim 9, wherein a solution containing the reagent for said luminescent reaction supplied to said channel contains glycerol.

13. The analysis method according to claim 9, wherein a solution containing the reagent for said luminescent reaction supplied to said channel contains glycerol in a range of 30% or more and 80% or less.

14. The analysis method according to claim 1, wherein optical detection is performed via a polarizing plate in said step of detection.

15. The analysis method according to claim 1, wherein optical detection is performed in said step of detection by moving an optical system including an optical window and said solid phase relative to each other in a longitudinal direction of said channel.

16. The analysis method according to claim 1, wherein said light blocking particles are black particles.

17. The analysis method according to claim 1, wherein said light blocking particles are particles containing a light blocking substance.

18. The analysis method according to claim 1, wherein said light blocking particles are black particles wrapped in polystyrene.

* * * * *